(12) United States Patent
Hinchey

(10) Patent No.: US 7,674,952 B2
(45) Date of Patent: Mar. 9, 2010

(54) STRESS-INDUCIBLE PLANT PROMOTERS

(75) Inventor: Brendan S. Hinchey, Mystic, CT (US)

(73) Assignee: Monsanto Technology LLC, St. Louis, MO (US)

( * ) Notice: Subject to any disclaimer, the term of this patent is extended or adjusted under 35 U.S.C. 154(b) by 50 days.

(21) Appl. No.: 11/803,410

(22) Filed: May 14, 2007

(65) Prior Publication Data
US 2008/0047039 A1 Feb. 21, 2008

Related U.S. Application Data

(60) Division of application No. 11/066,911, filed on Feb. 25, 2005, now abandoned, which is a continuation-in-part of application No. 10/739,565, filed on Dec. 18, 2003, now abandoned.

(60) Provisional application No. 60/435,987, filed on Dec. 20, 2002, provisional application No. 60/547,761, filed on Feb. 25, 2004.

(51) Int. Cl.
*C12N 15/82* (2006.01)
*A01H 5/00* (2006.01)
*A01H 5/10* (2006.01)

(52) U.S. Cl. .................. 800/287; 536/24.1; 435/320.1; 800/298

(58) Field of Classification Search ........................ None
See application file for complete search history.

(56) References Cited

U.S. PATENT DOCUMENTS

| 2004/0123347 A1 | 6/2004 | Hinchey et al. ............. 800/289 |
| 2007/0016976 A1* | 1/2007 | Katagiri et al. ............. 800/279 |
| 2007/0020621 A1 | 1/2007 | Boukharov et al. ........ 536/24.1 |

OTHER PUBLICATIONS

Franken P. et al. The duplicated chalcone synthase genes C2 and Whp (white pollen) of Zea mays are independently regulated; evidence for translational control of Whp expression by the Anthocyanin intensifying gene in. EMBO J. Sep. 1991;10(9):2605-12.*

Doferus R et al. Differential interactions of promoter elements in stress responses of the Arabidopsis Adh gene. Plant Physiol. Aug. 1994;105(4):1075-87.*

Wesley S.V. et al. Construct design for efficient, effective and high-throughput gene silencing in plants. Plant J. Sep. 2001;27(6):581-90.*

Boukharov et al., Seq. ID No. 14530 from Publication No. 2007/0020621, published Jan. 25, 2007.

Doferus et al., "Differential interactions of promoter elements in stress responses of the *Arabidopsis* Adh gene," *Plant Physiol.*, 105(4):1075-1087, 1994.

Iwasaki et al., "Identification of a cis-regulatory region of a gene in *Arabidopsis thaliana* whose induction by dehydration is mediated by abscisic acid and requires protein synthesis," *Mol. Gen. Genet.*, 247(4):391-398, 1995.

Kim et al., "A 20 nucleotide upstream element is essential for the nopaline synthase (nos) promoter activity," *Plant Mol. Biol.*, 24(1):105-117, 1994.

Mundy et al., "Abscisic acid and water-stress induce the expression of a novel rice gene," *EMBO J.*, 7(8):2279-2286, 1988.

Mundy et al., "Rice rab21 gene for water-stress inducible protein RAD21," GenBank Accession No. Y00842, Apr. 7, 1993.

Vilardell et al., "Gene sequence, developmental expression and protein phosphorylation of RAB-17 in maize," *Plant Molecular Biology*,14:423-432, 1990.

Wesley et al., "Construct design for efficient, effective and high-throughput gene silencing in plants," *Plant J.*, 27(6):581-590, 2001.

* cited by examiner

*Primary Examiner*—Cynthia Collins
(74) *Attorney, Agent, or Firm*—Erin C. Robert, Esq.; Sonnenschein Nath & Rosenthal LLP

(57) ABSTRACT

The present invention discloses and claims stress-inducible plant promoters, DNA constructs with such promoters, transgenic plants containing such promoters and DNA constructs, isolated DNAs encoding such promoters, and methods of making and using such promoters, DNA constructs, transgenic plants, and isolated DNAs.

10 Claims, 6 Drawing Sheets

FIGURE 1

TGCTTGCCCTTGTCCTCATGTACACAATCAGCTTGCTTATCTC
TCCCATACTGGTCGTTTGTTTCCCGTGGCCGAAATAGAAGAAG
ACAGAGGTAGGTTTTGTTAGAGAATTTTAGTGGTATTGTAGCC
TATTTGTAATTTTGTTGTACTTTATTGTATTAATCAATAAAGG
TGTTTCATTCTATTTTGACTCAATGTTGAATCCATTGATCTCT
TGGTGTTGCACTCAGTATGTTAGAATATTACATTCCGTTGAAA
CAATCTTGGTTAAGGGTTGGAACATTTTATCTGTTCGTGAAA
CATCCGTAATATTTTCGTTGAAACAATTTTATCGACAGCACC
GTCCAACAATTTACACCAATTTGGACGTGTGATACATAGCAGT
CCCCAAGTGAAACTGACCACCAGTTGAAGGTATACAAAGTGA
ACTTATTCATCTAAAAGACCGCAGAGATGGGCCGTGGGCCGTG
GCCTGCGAAACGCAGCGTTCAGGCCCATGAGCATTTATTTTTT
AAAAAAATATTTCACAACAAAAAGAGAACGGATAAAATCCAT
CGAAAAAAAAACTTTCCTACGCATCCTCTCCTATCTCCATCC
ACGGCGAGCACTCATCCAAACCGTCCATCCACGCGCACAGTAC
ACACACATAGTTATCGTCTCTCCCCCGATGAGTCACCACCCG
TGTCTTCGAGAAACGCCTCGCCCGACACCGTACGTGGCGCCAC
CGCCGCGCCTGCCGCCTGGACACGTCCGGCTCCTCTCCACGCC
GCGCTGGCCACCGTCCACCGGCTCCCGCACACGTCTCCCTGTC
TCCCTCCACCCATGCCGTGGCAATCGAGCTCATCTCCTCGCCT
CCTCCGGCTTATAAATGGCGGCCACCACCTTCACCTGCTTGCA
CACCACAGCAAGAGCTAAGTGAGCTAGCCACTGATCAGAAGAA
CACCTCGATCTCCGAGAGTTTTTTTTCAGCTTTAGCTTAAGCA
GG

FIGURE 2

```
TTTGATTTGGGACAAAAGGTTGGTGAAATGGACATATTTTCACATATATAT
ATGCTATATTTTCTTCTCAGTTTACCGAAAAGATGTACCCTTATATCTCGT
CATCGATTTTGGGTCAGGCCAGAAAACCATTGGTAACAGAATATATGCATA
GTTTTCTTTATCAATAAAATTAATGTTTTATTTAAAAATCGATAAAGGAACT
TTTTACAAAATTAGGCTAGAAATGGTCTGTCTATTATGACAAGGTAAACTT
TTGCGACATTAATTTGGATGGCAACTTCAACAATTCAAATTGTCGTTGTCC
ACAAATCTCTTGGTTGTAGAAGACCCACGCGTCTGCAACATTTTGCGCCG
AAAACTTAATACATAAACTTGATTTGTTGGGATACATGGTGCAGAAGATAC
GATCATTAATAATTCAAACAGTGCATTTCATGGTCCAACTGACTGCCACGT
CATTGAACCCGTAATCATTCGCTAAGCCAAATCAAATTGGCCTCAAATGAA
TTTTCAGCACGACTTTTTACGCCCCAAAAACCTAGTACTCCCTCCAGTTGG
AAATGTACCCTACCAAGAAACTTGTGTCCGTCACGACGCCTGTATCATCAA
TCTAGTCCTCTTTTGTAACAAAATAATTTTAGAAGATTTCTTTTAATGCCGT
AGAAATTAAATTAATCCTAATGAAAATCATGTAAAACTCACCCGTTATAAA
ATGTCACTAACCCCCTACACGGTTGGTGTCCTCTTTGTAGCCGAAATGCCT
CCTCTTTGGCCACTGCATCTCCACCCATTTTTCAAACATCTCCAACTAACTT
TTTGTTCCATTTGCAAAAATGCAAAATGCGAAATGTTAACTTCACACACAC
CCCCCTACCACTACAAAACTCTCACCAACCCCAATCTAGCTATCAGTTCAG
AAAGCACCTTCCCTTCTTTCCCTATTAGAGCAAGTCTAATAGTACAGCTCA
CTACTAGCTTCAATTTATCTATAACCAATCTAATAGTCAATTCATACAATA
GTTGCTTATTATACTATTAATATATGGTCTCACCTGTCATACACAGTGTG
TCTTATAGTCCGTGCTGCAGCTGGCTACATATCTGTAGCCTGCTAGTCTTCT
CTCTCATCGTTTATCTCATTAAAATATGTTTATAGCTGGCTAATAGCTTGCT
AATAGCATGCTATTGTACCTGCTCTTACCACCTTCTTTCCCTTTTGGCAAAT
GGCAATGAGTGCAAAAATGCTTGGAAAAATAACCCCCCCCCCCCACCCC
CACCTGATTATTTCCAGTAGGGCCAAAATCCGGGCCCACGTCCGCAACCCA
TGTGGGCCCCACATCCCCCACACCAACCCTCTGCACCCAAAATCCCCATCC
CCCCACTATATATAATCCCCGCCGTTGGATCATCGCCCTCAGCAGAGCAGC
GCATCTGCATCCAAAACCAAACCCAAACTCGTCTTCTCCACCGGAGCAGAG
CAGCGGCGGCGGCA
```

FIGURE 3

AATATACCATTCGCTAAAAAATTTGATTTTTCTATGACGGAGA
AAGCAGTAGTGTAAGCAGAGCGCCCGTAAACATATCCTCACTT
TTGGTTCATCTCATATTTTTGTAAGATGGAGGAAACATGAGTG
AAATTAGAGCACCCTGTAAACATATCCTCATTTTGGTTCGTCT
ATCAGTCACGTAACTTTGTTATTTCTGTCGGTTACCTAGTACT
AATACCTAAGATGATAATCCACTGTAATGGGAAGATGAGCACG
GTTTTATATCTGAAACTGAAATGGGTCTGTTGGTCATAAAAC
TTACTACCTCCGTTTCGAAATATATCAAACTAGCTTGTATTAG
ATTAGACACGATCTATTATTCAATTTGGACAGAGTCCATATAG
CTATGATATGCTTACTATTTCATATTGCTTTCATGAACTTAAC
TTAAAGTTTTGGACCACAATGAAAGTTTCAGTTCATATCATAT
GGCATACTACTTCTATTCTTTTTTTTTTGTTAAAAAAAACTG
GAGCTCTCAATTTTTTTAAAGTTTGTCCTGTTACAATTTTAAT
CAGTTCTTTATTATTCCTCTCCACATCAACAATTTTTCCTCGA
TGATCCGGTTCCCTTTTGACCTCACTGCACTGTCCAGATCTC
TCATTAATCCAACCCAGAAAAAAAAAACAGTACAAAATAAAAT
ACACAAGATTCAACAAAGCAACCTGACCTGGTCGGTGCTGTAC
CACGTGGCATCTCCCTCCATGTCCAATCACTTCGAGAGACA
AAAGAAACACTCCTCCAGTGGCATCCTGCCATGTGTCCTCCAT
TCTTGTACTTAATCTCTTCTTATTTAAGGCCTCATAATCTCTT
GCTTTCCCTTCCCTAGTAAATCAAAGAACACAAAGCATCCAAA
ACAACACCAGGAAACTTCTTTTCAATCGATCACTCCACTGGTG
AGTAGTGAGTGGCTAGTGACTGGTCAGTTCATCACTTGTGAAG
GTTTTGCAATCAGGAAAAGTTCAGAAGATC

FIGURE 4

```
TAGCATATATAAAATCATTTGTCAGAGTGAAACAACACATCCA
AATTAATGACAAATATAAATTACTAATCTACTTTGATCCATCT
CATCATTTTAAAGAAAATACTAAAATCCATTAAAAGATCATT
TTGGAAAATTAAACTTTTATTGAAAATAAACTAACTCATGTAA
AATTATACCGTTTTCCTGTTACATGTACAGGATATAAATTAAC
AGCGCCTTTTGGCGCGCTGATTTTCTAGTCGAAAGTTAAA
CCGGGGTATAAGTGTAGCACCTTCGCTCCACTCAAAGAAAATG
TAAGCCGAAGACTTGAGAAGCTTCCAGAATCCAGAGATCGCAG
CAGAAAAGGAGCGAACAAGGCAAACCTCTCAAAGGAAAAAGA
AAAATAATAAAGGAGGAAACCTGTCAAACACCACCCTATGACA
AGTGGGTCCCACTCGAACCAACCGTACGGCCCCCCACCCAAA
CCCGCTCCCCCCTCGCTCCGAAATATCCACCTCTCTAGATCT
TTCTCGTCGCAAACGCCCTTCCGCCCCGCCTCGCCGCGCCCA
TTCCACCACCTTTCCGAACCTTCCACTCCCTTCCAGACTCCAC
CCCCACGTCACCCCTATTTAAACCCTCCTCCCACCGAGCAAT
CAAGCGACAAGATCGAGAAGCCACAAACCCAGCGCGATCCGA
GGTAGAAGAAGAAGAAGAAGAAGAAGAAGAGGCGATCGAG
AG
```

FIGURE 5

GTTCGTGACTTTTGGCAAGGGATCGAATCGGAAGCGAATGGGT
GGGCCCAAAACGGGCCGGTTATTTTACTGGGACTAAAGATATC
GGCCCATCTGAATTGTGCGTTCCGCCGGATAAGGGATAACTGA
AGGCGGCGCTCAGTCCCGCGCCTTCTGGAACCTTCCCGTGGAA
GGGGCATACAGCCTTGCAGCGGCAGCTTCCGGAAGCTTCTGAA
TTCTTCTCCAAGATTTGCCGCGACGATAAATCCTCTCGTTTCT
CCGCTCGCTGATTCATTCTAACGCAAATCCAAAAGATAAGC
ACAGTTACGCGGCGAGAGCGAGAGAGGAGTGGAGAGCC

FIGURE 6

```
AAAACCTCTTCTTTAACATGTAAACGACCTGGAGGATGTCAAC
TCTGACACGCTGGCGAAATCATCCACCTATGTCTTTGCCGCGG
TATAGGATGAACATGGGTAGAGAAAAAATCGGGGTGATCCAA
AGTGCAATAGACGTGACCCAAAAAGTGTAATTCACTAAAAAA
ACTTACCAACGAAGCAATGCTTTGGCAGTGATTTTTACCTTTC
AGTCATGGGCATGACCTGCATTGTAAATAACGTGGTTGTGAA
TTCAAACTCAATGTGTTTTCTTTCACAAGTTGCCGTTAAAA
ATATGTTTCGCAAGAGACTCACTGCTCCCAGTGAAAGCAGTGA
ATTGAAGCATTCCCGAAACCCACTGGAATGATCTAGTACTCAC
TCTACGATGTACAGTGAAGTAATACTTCAAAACTGGTGTAATT
TGGTATGCCAAAAGGACTCCATAGTTTCACGACATATTTCCAA
ACGGTTCAGGATCAGTACTGCCCATCTGCCTGGGGCCCACACT
AGCGGGCAATTGGTTCTCGTAGTTTCTCGTTCTCAATCAATCA
TTCCATACTCGCTATCCCCTCCATCACAGAATAAATGCAACAA
TGAGTTTCGTGTACAAATTTAATCGTTCGTCTTATTTAAAAT
ATTTTTTAAAAAACTAAAAAACAAAGTCACGCATAAAGTACT
ATTCATGTTTTATAATCTAATAACAGTATAAATACTAATCATA
AAAAAAAATTCAAATAAGATGGACGATTAAAGTTGAACACTGA
AATTCATGGCTGCTTTTGTTTTGAGACTGAGGGAGTACACGAT
AAGATTTGATCGCAATCAAAGTAACCTACATCAAAGAAGCAAG
ATATGTGGGGAAAAATGAATACTCTAGAGCAAATTAAGGTGA
GCCCGCTTTGTAGAGGCTGATGGAGTACTGGAGCGACGGAAG
CGAAGCAGATCGAGTGTGCTGTAAAGCGAAACGAGCAAGAACC
AGAGAAGTCCAGAGATTTCAGGACAGATTAGTTGTGAACCTAT
AAATATCCTGCCTCATTCCCCAACCTCCATCCATCGAGCCAAG
ACTGAAGCATTTGATCGAGCTCCAAACAAACACTCGTTCCAAA
CTTCCTCCAATCCACTTCATACAAGAAACCTAAGCAGCTAGC
GATCCACGACAAACCAACA
```

STRESS-INDUCIBLE PLANT PROMOTERS

This application is a Divisional of U.S. patent application Ser. No. 11/066,911 filed 25 Feb. 2005 now abandoned and published as U.S. Patent Application Publication US20050155114, which is a Continuation-in-Part of U.S. patent application Ser. No. 10/739,565 to Hinchey et al. filed 18 Dec. 2003 now abandoned and published as U.S. Patent Application Publication 2004/0123347, which claims priority to U.S. Provisional Patent Application No. 60/435,987, filed 20 Dec. 2002, both of which are incorporated by reference in their entirety herein; and further claims the benefit of priority of U.S. Provisional Patent Application No. 60/547,761, filed 25 Feb. 2004; all disclosures of which are incorporated by reference in their entirety herein.

INCORPORATION OF SEQUENCE LISTING

The sequence listing contained in the file named pa_01299, which is 7,854 kilobytes (as measured in MS Windows®) and located in computer readable form on a compact disk created on 7 May 2007, is filed herewith and incorporated herein by reference.

FIELD OF THE INVENTION

The present invention relates generally to molecular biology, and more particularly to plant promoters useful, for example, in agricultural biotechnology.

BACKGROUND OF THE INVENTION

Stress (for example, water deficit, cold, heat, salt, pest, disease, or nutrient stress), can have adverse effects on plants such as yield reductions, increased susceptibility to disease and pests, reduced plant growth, and reproductive failure. An object of this invention is to provide transgenic plants which can express genes to ameliorate the adverse effects of stress. Useful genes for expression under stress are genes which promote aspects of plant growth or fertility, genes which impart disease or pest resistance or tolerance, stress-responsive transcription factors, and the like.

As a non-limiting example, considering the complexity of water use in land plants, especially during conditions that produce water deficit, relatively few promoters specifically associated with this aspect of plant physiology have been identified. It would be of benefit to the art to increase the known number and variety of promoters involved in the response to stress (such as the response to water deficit, cold, heat, salt, pest, disease, or nutrient stress) in plants, particularly in economically important plants (such as crop plants, for example, maize), and even more particularly in plants experiencing such stress. It would be especially advantageous to identify promoters which can be used in directing the expression of genes which are beneficial to the plant when induced during conditions of stress (for example, induced under conditions of water deficit, while having low to no expression under adequately watered conditions).

SUMMARY OF THE INVENTION

The present invention discloses stress-inducible plant promoters, DNA constructs with such promoters, transgenic plants containing such promoters and DNA constructs, isolated DNAs encoding such promoters, and methods of making and using such promoters, DNA constructs, transgenic plants, and isolated DNAs.

The present invention discloses and claims an isolated DNA including:
a) about 100 to about 950 contiguous nucleotides of DNA, wherein the contiguous nucleotides of DNA have from 85% to 100% sequence identity to at least one segment of SEQ ID NO:1, or
b) about 100 to about 1500 contiguous nucleotides of DNA, wherein the contiguous nucleotides of DNA have from 85% to 100% sequence identity to at least one segment of SEQ ID NO:2, or
c) about 100 to about 1000 contiguous nucleotides of DNA, wherein the contiguous nucleotides of DNA have from 85% to 100% sequence identity to at least one segment of SEQ ID NO:3, or
d) about 100 to about 700 contiguous nucleotides of DNA, wherein the contiguous nucleotides of DNA have from 85% to 100% sequence identity to at least one segment of SEQ ID NO:4, or
e) about 100 to about 300 contiguous nucleotides of DNA, wherein the contiguous nucleotides of DNA have from 85% to 100% sequence identity to at least one segment of SEQ ID NO:5, or
f) about 100 to about 1100 contiguous nucleotides of DNA, wherein the contiguous nucleotides of DNA have from 85% to 100% sequence identity to at least one segment of SEQ ID NO:6.

The isolated DNA of the invention has utility in and of itself, for example, as a material useful in assaying plants and other organisms for the presence of nucleic acid sequences identical or substantially identical to the claimed isolated DNA or for locating nucleic acid sequences adjacent to a sequence contained within an isolated DNA of the invention. Such assays are known in the art, and can include, for example, assays involving nucleic acid hybridization probes or primers. The isolated DNA may be used as an intact sequence as provided by any of SEQ ID NO:1, SEQ ID NO:2, SEQ ID NO:3, SEQ ID NO:4, SEQ ID NO:5, and SEQ ID NO:6, or as a fragment of such sequences. The length and percent identity of such fragments can be varied according to the intended application, for example, length may be increased, or percent identity required to be high (e. g., greater than about 90%, about 95%, about 98%, or even 100% sequence identity) to obtained increased stringency requirements for hybridization. Shorter fragments can be useful as primers, as is well known in the art.

The isolated DNA of the invention, when introduced appropriately into a plant, preferably has promoter activity in plants under conditions of stress (for example, water deficit, cold, heat, salt, pest, disease, or nutrient stress, and the like). The disclosed promoters are derived from the 5' regulatory region of rice genes identified as a rab17 gene (RAB17), a cinnamic acid 4-hydroxylase (CA4H) gene (CA4H), an HVA22 gene (HVA22), and genes for heat shock proteins 17.5 (HSP17.5), 22 (HSP22) and 16.9 (HSP16.9). In one embodiment of the invention the promoters are derived from the 5' regulatory region of a rice RAB17 gene and have a nucleotide sequence identical or substantially identical to at least one segment of SEQ ID NO:1. In yet another embodiment of the invention the promoters are derived from the 5' regulatory region of a rice CA4H gene and have a nucleotide sequence identical or substantially identical to at least one segment of SEQ ID NO:2. In yet another embodiment of the invention the promoters are derived from the 5' regulatory region of a rice HVA22 gene and have a nucleotide sequence identical or substantially identical to at least one segment of SEQ ID NO:3. In yet another embodiment of the invention the promoters are derived from the 5' regulatory region of a rice HSP17.5 gene and have a nucleotide sequence identical or substantially identical to at least one segment of SEQ ID NO:4. In yet another embodiment of the invention the promoters are derived from the 5' regulatory region of a rice HSP22 gene and have a nucleotide sequence identical or substantially identical to at least one segment of SEQ ID NO:5. In yet another embodiment of the invention the promoters are derived from the 5' regulatory region of a rice HSP16.9 gene and have a nucleotide sequence identical or substantially identical to at least one segment of SEQ ID NO:6. The present invention further provides stress-inducible promoters from plants other than rice and derived from the 5' regulatory regions of homologs of the rice RAB17, CA4H, HVA22, HSP17.5, HSP22, or HSP16.9 genes. Thus, one aspect of the invention is broadly directed to stress-inducible promoters for use in plants, and is illustrated by the more specific reference to the stress-inducible character of the disclosed and claimed promoters. One particular aspect of the present invention is directed to water-deficit-inducible promoters which exhibit promoter activity in plant tissue having a water potential of less than about −0.7 megaPascals (MPa), e. g., at less than about −0.8 MegaPascals or lower, such as less than about −0.9 MegaPascals or less than about −1.0 MegaPascals.

The present invention further discloses and claims an exogenous DNA construct including a promoter of the present invention operably linked to a heterologous DNA, transgenic plants containing such an exogenous DNA construct, and methods for making such transgenic plants. In particular, the present invention provides a DNA construct including a promoter operably linked to a heterologous DNA, wherein the promoter includes:

a) about 100 to about 950 contiguous nucleotides of DNA, wherein the contiguous nucleotides of DNA have from 85% to 100% sequence identity to at least one segment of SEQ ID NO:1, or b) about 100 to about 1500 contiguous nucleotides of DNA, wherein the contiguous nucleotides of DNA have from 85% to 100% sequence identity to at least one segment of SEQ ID NO:2, or c) about 100 to about 1000 contiguous nucleotides of DNA, wherein the contiguous nucleotides of DNA have from 85% to 100% sequence identity to at least one segment of SEQ ID NO:3, or d) about 100 to about 700 contiguous nucleotides of DNA, wherein the contiguous nucleotides of DNA have from 85% to 100% sequence identity to at least one segment of SEQ ID NO:4, or e) about 100 to about 300 contiguous nucleotides of DNA, wherein the contiguous nucleotides of DNA have from 85% to 100% sequence identity to at least one segment of SEQ ID NO:5, or f) about 100 to about 1100 contiguous nucleotides of DNA, wherein the contiguous nucleotides of DNA have from 85% to 100% sequence identity to at least one segment of SEQ ID NO:6.

Thus, the present invention provides DNA constructs with stress-inducible promoters for expressing heterologous DNA in plants during conditions of stress (for example, water deficit, or other stresses such as cold, heat, salt, pest, disease, or nutrient stress). One aspect of the invention provides a DNA construct including a promoter operably linked to a heterologous DNA, where the promoter is derived from the 5' regulatory region of a rice RAB17, CA4H, HVA22, HSP17.5, HSP22, or HSP16.9 gene and exhibits promoter activity. Thus, one aspect of the invention provides a DNA construct including a promoter operably linked to a heterologous DNA, where the promoter includes a nucleic acid sequence from any of SEQ ID NO:1, SEQ ID NO:2, SEQ ID NO:3, SEQ ID NO:4, SEQ ID NO:5, and SEQ ID NO:6. A further aspect of the invention provides a DNA construct including a promoter operably linked to a heterologous DNA, where the promoter includes at least 100 contiguous nucleotides which are identical or substantially identical to (that is to say, has at least about 85% sequence identity with) at least one segment of any of SEQ ID NO:1, SEQ ID NO:2, SEQ ID NO:3, SEQ ID NO:4, SEQ ID NO:5, and SEQ ID NO:6, or a larger identical or substantially identical segment, e. g., about 125 nucleotides, about 300 nucleotides, about 500 nucleotides, about 750 nucleotides or more, as is described in further detail herein. Yet another aspect of the invention provides a DNA construct including a promoter of the invention, operably linked to a heterologous DNA which encodes a molecule imparting at least one characteristic selected from the group consisting of insect resistance or tolerance; viral, bacterial, fungal, or nematode disease resistance or tolerance; herbicide resistance or tolerance; enhanced grain composition or quality; enhanced nutrient transporter functions; enhanced nutrient utilization; enhanced environmental stress tolerance or resistance; reduced mycotoxin contamination; male sterility; female sterility; a selectable marker phenotype; a screenable marker phenotype; a negative selectable marker phenotype; a stress-responsive transcription factor; altered plant agronomic characteristics; enhanced kernel development; enhanced embryo development; enhanced general production or protection of next-generation tissues; enhanced grain agronomic characteristics; enhanced grain processing characteristics; and a combination thereof.

The present invention further discloses and claims a transgenic plant having in its genome an exogenous DNA construct of the invention, that is to say, an exogenous DNA construct including a promoter operably linked to a heterologous DNA, wherein the promoter exhibits stress-inducible promoter activity and includes:

a) about 100 to about 950 contiguous nucleotides of DNA, wherein the contiguous nucleotides of DNA have from 85% to 100% sequence identity to at least one segment of SEQ ID NO:1, or b) about 100 to about 1500 contiguous nucleotides of DNA, wherein the contiguous nucleotides of DNA have from 85% to 100% sequence identity to at least one segment of SEQ ID NO:2, or c) about 100 to about 1000 contiguous nucleotides of DNA, wherein the contiguous nucleotides of DNA have from 85% to 100% sequence identity to at least one segment of SEQ ID NO:3, or d) about 100 to about 700 contiguous nucleotides of DNA, wherein the contiguous nucleotides of DNA have from 85% to 100% sequence identity to at least one segment of SEQ ID NO:4, or e) about 100 to about 300 contiguous nucleotides of DNA, wherein the contiguous nucleotides of DNA have from 85% to 100% sequence identity to at least one segment of SEQ ID NO:5, or f) about 100 to about 1100 contiguous nucleotides of DNA, wherein the contiguous nucleotides of DNA have from 85% to 100% sequence identity to at least one segment of SEQ ID NO:6.

Thus, this invention provides transgenic plants with a stress-inducible promoter operably linked to heterologous DNA, e. g., a gene of interest. More particularly such a transgenic plant contains in its genome a DNA construct according to this invention, e. g., a DNA construct including a promoter operably linked to heterologous DNA where the promoter is derived from the 5' regulatory region of a rice RAB17, CA4H, HVA22, HSP17.5, HSP22, or HSP16.9 gene. The transgenic plant may be any monocot or dicot plant of interest, including, but not limited to, plants of commercial or agricultural interest, such as crop plants, wood- or pulp-producing trees, vegetable plants, fruit plants, and ornamental plants. Non-limiting examples of plants of interest include crop plants such as wheat, oat, barley, maize, rye, triticale, rice, ornamental and forage grasses, sorghum, millet, sugarcane, coconut, oil palm, date palm, olive, tree nuts (such as walnut, cashew, hazelnut, pecan, almond, and the like), canola, cotton, safflower, soybean, sugarbeet, buckwheat, sunflower, tea, and coffee; wood- or pulp-producing trees; vegetable crop plants such as legumes (for example, beans, peas, lentils, alfalfa, peanut), lettuce, asparagus, artichoke, celery, carrot, radish, amaranth, the brassicas (for example, cabbages, kales, mustards, and other leafy brassicas, broccoli, cauliflower, Brussels sprouts, turnip, kohlrabi), edible curcubits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (beet, chard, spinach, quinoa); fruit crop plants such as apple, pear, citrus fruit (orange, lime, lemon, grapefruit, and others), apricot, peach, plum, nectarine, banana, pineapple, grape, kiwifruit, papaya, avocado, and berries; and ornamental plants including ornamental flowering plants, ornamental trees and shrubs, and ornamental groundcovers. Preferred monocot plants include, but are not limited to, wheat, oat, barley, maize, rye, triticale, rice, ornamental and forage grasses, sorghum, millet, and sugarcane, more preferably maize, wheat, and rice. Preferred dicot plants include, but are not limited to, canola, cotton, potato, quinoa, amaranth, buckwheat, safflower, soybean, sugarbeet, and sunflower, more preferably soybean and cotton.

The present invention also provides for a transgenic plant including a stress-inducible promoter (such as a promoter inducible by water deficit, cold, heat, salt, pest, disease, nutrient, or other environmental stress), in combination with an enhancer, for example, an intron. In one embodiment, the enhancer intron is a rice actin 1 intron 1 or a rice actin 2 intron 1. The promoter element may further include a 3' untranslated region (3' UTR), such as a nos or T7 3' UTR.

In one embodiment of the invention, the transgenic plant includes a DNA construct with a heterologous DNA operably linked to a native or exogenous stress-inducible promoter or a derivative of a native or exogenous stress-inducible promoter, such as are disclosed by the invention. In one non-limiting and more particular embodiment of the invention, the transgenic plant includes a DNA construct with a heterologous DNA operably linked to a native or exogenous water-deficit-inducible promoter or a derivative of a native or exogenous water-deficit-inducible promoter. Preferred heterologous DNA includes genes that are effective in or needed by a plant during water deficit, cold, heat, salt, pest, disease, nutrient, or other environmental stress, for plant growth or survival. Potentially any heterologous DNA can be operably linked to the stress-inducible promoter, including a selected sequence which encodes a molecule imparting at least one characteristic selected from the group consisting of insect resistance or tolerance; viral, bacterial, fungal, or nematode disease resistance or tolerance; herbicide resistance or tolerance; enhanced grain composition or quality; enhanced nutrient transporter functions; enhanced nutrient utilization; enhanced environmental stress tolerance or resistance; reduced mycotoxin contamination; male sterility; female sterility; a selectable marker phenotype; a screenable marker phenotype; a negative selectable marker phenotype; a stress-responsive transcription factor; altered plant agronomic characteristics; enhanced kernel development; enhanced embryo development; enhanced general production or protection of next-generation tissues; enhanced grain agronomic characteristics; enhanced grain processing characteristics; and a combination thereof. In preferred aspects of this invention the stress-inducible promoter is operably linked to heterologous DNA which encodes a molecule imparting enhanced environmental stress tolerance, such as, but not limited to, water deficit tolerance, salinity tolerance, cold tolerance, heat tolerance, and the like. One non-limiting embodiment of this invention includes a water-deficit-inducible promoter operably linked to heterologous DNA which encodes a molecule imparting enhanced water deficit tolerance.

The selected heterologous DNA may further include DNA from a cloning vector (such as DNA from a plasmid or any other suitable vector) or, alternatively, may have been introduced as an expression cassette isolated from such vector DNA. The selected DNA may also include a sequence encoding a signal peptide as are known in the art. Examples of signal peptides that could be used include, but are not limited to, subcellular targeting peptides such as a peroxisomal targeting peptide or a chloroplast transit peptide. Examples of a chloroplast transit peptide include the group consisting of chlorophyll a/b binding protein transit peptide, small subunit of ribulose bisphosphate carboxylase transit peptide, EPSPS transit peptide, and dihydrodipocolinic acid synthase transit peptide.

The transgenic plants of the invention preferably express DNA of interest during conditions of stress (for example, water deficit, cold, heat, salt, pest, disease, nutrient, or other environmental stress). Thus, this invention discloses and claims a method for providing a plant which expresses a gene of interest under conditions of stress, including introducing into the genome of the plant a DNA construct including a stress-inducible promoter operably linked to heterologous DNA desired to be expressed during stress. In one preferred, non-limiting embodiment, such a plant has a water-deficit-inducible promoter which exhibits promoter activity in plant tissue having a water potential of less than −0.7 megaPascals, e.g., at less than about −0.8 MegaPascals or lower, such as less than about −0.9 MegaPascals or about −1.0 MegaPascals.

A transgenic plant prepared in accordance with the invention may be of any generation, including a fertile R0 transgenic plant as well as progeny plants of any generation of interest and hybrid progeny plants thereof which contain the heterologous DNA. Also included within the invention are seeds of any such plants.

In yet another aspect, the invention provides a method of plant breeding including the steps of: (i) obtaining a transgenic plant including a stress-inducible promoter (such as a promoter inducible by water deficit, cold, heat, salt, pest, disease, nutrient, or other environmental stress) of this invention and (ii) crossing the transgenic plant with itself or a second plant. The transgenic plant may be of any species of interest, including monocotyledonous or dicotyledonous plants.

Other specific embodiments of the invention are disclosed in the following detailed description.

BRIEF DESCRIPTION OF THE DRAWINGS

FIG. 1 depicts 991 base pairs (bp) of DNA sequence comprising a 5' regulatory region of a rice RAB17 gene (SEQ ID NO:1).

FIG. 2 depicts 1500 bp of DNA sequence comprising a 5' regulatory region of a rice CA4H gene (SEQ ID NO:2).

FIG. 3 depicts 1019 bp of DNA sequence comprising a 5' regulatory region of a rice HVA22 gene (SEQ ID NO:3).

FIG. 4 depicts 733 bp of DNA sequence comprising a 5' regulatory region of a rice HSP17.5 gene (SEQ ID NO:4).

FIG. 5 depicts 339 bp of DNA sequence comprising a 5' regulatory region of a rice HSP22 gene (SEQ ID NO:5).

FIG. 6 depicts 1180 bp of DNA sequence comprising a 5' regulatory region of a rice HSP16.9 gene (SEQ ID NO:6)

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Where a term is provided in the singular, the inventors also contemplate aspects of the invention described by the plural of that term. The nomenclature used herein and the laboratory procedures described below are those well known and commonly employed in the art. Where there are discrepancies in terms and definitions used in references that are incorporated by reference, the terms used in this application shall have the definitions given herein. Other technical terms used herein have their ordinary meaning in the art that they are used, as exemplified by a variety of technical dictionaries. The inventors do not intend to be limited to a mechanism or mode of action. Reference thereto is provided for illustrative purposes only.

DEFINITIONS

As used herein, "coding sequence" means a DNA sequence which directs the production of an RNA molecule. The RNA may be an mRNA, which encodes a protein product, or a tRNA, rRNA, snRNA, antisense RNA, or other RNA molecule.

As used herein, "exogenous DNA" refers to DNA which is not normally found next to the adjacent native DNA, i. e., a sequence not normally found in the host genome in an identical context. The DNA itself may be native to the host genome or may comprise the native sequence altered by the addition or deletion of one or more different regulatory elements or other sequences. The exogenous DNA may encode a protein or non-protein product. Likewise, "exogenous sequence" is a sequence of DNA not normally found in the host genome in an identical context. A transformation construct comprising a gene of interest, which originates or is produced outside of an organism, is an example of an exogenous DNA.

As used herein, "expression" refers to the combination of intracellular processes, including transcription and translation, undergone by a DNA molecule, such as by a structural gene to produce a polypeptide, or by a non-structural gene to produce an RNA molecule.

As used herein, "gene" means a DNA sequence from which an RNA molecule is transcribed. The RNA may be, for example, an mRNA which encodes a protein product, an mRNA that encodes a DNA aptamer, an RNA which functions as an anti-sense molecule, an RNA aptamer, or a structural RNA molecule such as a tRNA, rRNA or snRNA, or other RNA.

As used herein, "heterologous" DNA is any DNA sequence which is not naturally found next to the adjacent DNA. Heterologous DNA is often found in a DNA construct used for transformation. A water-deficit-inducible promoter of the instant invention, e. g., RAB17, operably linked to a reporter gene, is an example of a heterologous DNA as the RAB17 promoter is naturally and normally associated with a RAB17 gene.

As used herein, "progeny" means any subsequent generation, including the seeds and plants therefrom, which is derived from a particular parental plant or set of parental plants; the resultant progeny line may be inbred or hybrid. Progeny of a transgenic plant of this invention can be, for example, self-crossed, crossed to a transgenic plant, crossed to a non-transgenic plant, and/or back-crossed.

As used herein, "promoter" means a region of DNA sequence that is essential for the initiation of transcription of RNA from DNA. Promoters generally are located upstream of the translated DNA and have regions that act as binding sites for RNA polymerase and can have regions that work with other factors to promote RNA transcription. More specifically, basal promoters in plants comprise canonical regions associated with the initiation of transcription, such as CAAT and TATA boxes. The TATA box element is usually located approximately 20 to 35 nucleotides upstream of the site of initiation of transcription. The CAAT box element is usually located approximately 40 to 200 nucleotides upstream of the start site of transcription. The location of these basal promoter elements result in the synthesis of an RNA transcript comprising nucleotides upstream of the translational ATG start site. The region of RNA upstream of the ATG is commonly referred to as a 5' untranslated region or 5' UTR. Standard molecular biology techniques can be used to make novel combinations of basal promoters, that is to say, novel promoter sequences comprising, for example, sequences from the CAAT box to the translational start site, with other upstream promoter elements to enhance or otherwise alter promoter activity or specificity.

As used herein, "promoter activity" refers to the activity that characterizes a DNA sequence which initiates transcription of RNA from adjacent downstream DNA.

As used herein, an "R0 transgenic plant" is a plant which has been directly transformed with a selected DNA or has been regenerated from a cell or cell cluster which has been transformed with a selected DNA.

As used herein, "regeneration" refers to the process of growing a plant from a plant cell or cells (e. g., plant protoplast, callus, or explant).

As used herein, "transformation construct" means a DNA molecule which is designed for introduction into a host genome by genetic transformation. Preferred transformation constructs comprise all of the genetic elements necessary to direct the expression of one or more exogenous sequences. Transformation constructs prepared in accordance with the instant invention can include, for example, a rice RAB17, CA4H, HVA22, HSP17.5, HSP22, or HSP16.9 promoter, or novel promoters derived from these sequences. In certain embodiments of the instant invention, it may be desirable to introduce a transformation construct into a host cell in the form of an expression cassette.

As used herein, "transgene" means a segment of DNA which has been incorporated into a host genome or is capable of autonomous replication in a host cell, and is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

As used herein, "transgenic plant" means a plant or progeny plant of any subsequent generation derived therefrom, wherein the DNA of the plant or progeny thereof contains an introduced exogenous DNA segment not originally present in a non-transgenic plant of the same strain. The transgenic plant may additionally contain sequences which are native to the plant being transformed, but wherein the "exogenous" gene has been altered in order to alter the level or pattern of expression of the gene.

As used herein, a "stably" transformed plant is a plant in which the exogenous DNA is heritable. The exogenous DNA may be heritable as a fragment of DNA maintained in the plant cell and not inserted into the host genome. Preferably, the stably transformed plant comprises the exogenous DNA inserted into the chromosomal DNA in the nucleus, mitochondria, or chloroplast, most preferably in the nuclear chromosomal DNA.

As used herein, "water deficit" is a plant condition characterized by water potential in a plant tissue of less than about −0.7 MegaPascals, e. g., about −0.8 MegaPascals. Water potential in maize is conveniently measured by clamping a leaf segment in a pressurizable container so that a cut cross-section of leaf is open to atmospheric pressure. Gauge pressure (above atmospheric pressure) on the contained leaf section is increased until water begins to exude from the atmospheric-pressure-exposed cross-section; the gauge pressure at incipient water exudation is reported as negative water potential in the plant tissue, e. g., 0.7 MegaPascals gauge pressure is reported as −0.7 MegaPascals water potential.

As used herein, "isolated DNA" or "isolated nucleic acid" refers to a targetted DNA or nucleic acid sequence that is substantially isolated or purified from other cellular or subcellular materials (for example, proteins, lipids, or DNAs or nucleic acids other than the targetted DNA or nucleic acid sequence). Such an isolated or purified DNA or nucleic acid can be prepared, according to the intended application, to varying degrees of isolation or purity (for example, greater than about 70%, about 80%, about 90%, about 95%, about 98%, about 99%, or even higher purity), as is well known and practiced in the art. See, for example, Sambrook and Russell, "Molecular Cloning: A Laboratory Manual", third edition, Cold Spring Harbor Laboratory Press, 2001, 2344 pages, which is incorporated by reference herein, or the equivalent protocols available on line at molecularcloning.com.

As used herein "gene suppression" means any of the well-known methods for suppressing an RNA transcript or production of protein translated from an RNA transcript, including post-transcriptional gene suppression and transcriptional suppression. See, for example, Matzke et al. (2001) *Curr. Opin. Gen. Dev.*, 11:221-227 (2001), and Meister & Tuschl (2004) *Nature*, 431:343-349, which are incorporated by reference herein. Post-transcriptional gene suppression is believed to be mediated by double-stranded RNA having homology to a gene targeted for suppression. Gene suppression by RNA transcribed from an exogenous DNA construct including an inverted repeat of at least part of a transcription unit is a common feature of gene suppression methods known variously as anti-sense suppression, co-suppression, and RNA interference. Transcriptional suppression can also be mediated, for example, by a transcribed double-stranded RNA having homology to promoter DNA sequence to effect what is called promoter trans-suppression. Gene suppression under a given stress condition can also be obtained by means of a DNA or RNA aptamer driven by a promoter of the present invention, as is known in the art (see, for example, Toulme et al. (2004) *FEBS Lett.*, 567: 55-62, Lee, et al. (2004) *Nucleic Acids Res.*, 32:95-100, and Nimjee et al. (2005) *Ann. Rev. Med.*, 56:555-583, which are incorporated herein by reference in their entirety).

Stress-Inducible Promoters

Plants from a number of maize lines were field-grown under non-irrigated (water-deficit-producing) or irrigated conditions. Leaf samples were taken from plants before the tassel stage for each field condition to allow measurement of water potential and isolated of RNA. Messenger RNAs (mRNAs) from stress (water deficit) and non-stress (non-water-deficit) samples were analyzed for differences using transcriptional profiling array methods. A number of mRNAs were found to show differences in accumulation, to either higher or lower levels in the plants, depending upon the water treatment.

Array samples were selected that demonstrated at least a 3-fold increase in mRNA accumulation in water-deficit-stressed plants. The water-deficit-inducible maize genes were identified as a RAB17 protein gene (RAB17), a gene encoding cinnamic acid 4-hydroxylase (CA4H), an HVA22 gene (HVA22), and heat shock protein 17.5 (HSP17.5), 22 (HSP22) and 16.9 (HSP16.9) genes (described in detail in U.S. patent application Ser. No. 10/739,565 to Hinchey et al., filed 18 Dec. 2003 and published as U.S. Patent Application Publication Number 2004/0123347, incorporated herein by reference in its entirety).

HSP17.5, HSP22 and HSP16.9 are three of a number of low molecular weight heat shock proteins identified in plants. Heat shock genes, first identified by response to conditions of thermal stress (elevated temperatures) in *Drosophila*, have been identified in a wide variety of organisms, including plants. HVA22 is one of many stress-induced genes known in plants, and homologues of this gene have been described in barley, *Arabidopsis*, and other plants. HVA22 has been described as being responsive to abscisic acid (ABA); promoter analysis of barley clones has identified a number of ABA response elements, as well as other associated sequences in the promoter, which affect and allow for hormonal response. CA4H is a member of the cytochrome P450 monooxygenase superfamily. It is thought to play a role in phenylpropanoid metabolism and lignin biosynthesis in plants. Promoters have been isolated for *Arabidopsis* CA4H, and while a number of putative cis-acting elements have been identified, matches to such elements are not evident in the promoter sequence of maize CA4H which is useful in this invention. Rab17 is a gene isolated from maize that is ABA-responsive as well as water deficit-responsive (Vilardell et al., *Plant Molecular Biology*, 17(5):985-993, 1990), and that was also identified in the water deficit screen described above.

Sequence comparison tools were used to identify promoters from rice genes homologous to the maize genes described in U.S. patent application Ser. No. 10/739,565 to Hinchey et al., filed 18 Dec. 2003 and published as U.S. Patent Application Publication Number 2004/0123347, which is incorporated by reference herein. Genomic DNA sequences from rice and maize genes were compared using comparison tools known to those in the art, such as, but not limited to, BLAST (Altschul et al. (1997) *Nucleic Acids Res.* 25:3389-3402, which is incorporated by reference herein), and the upstream regions of rice genes homologous to the maize RAB17, CA4H, HVA22, HSP17.5, HSP22, or HSP16.9 genes were selected. In this way, stress-inducible rice promoters were identified for RAB17 (SEQ ID NO:1), CA4H (SEQ ID NO:2), HVA22, (SEQ ID NO:3), HSP17.5 (SEQ ID NO:4), HSP22 (SEQ ID NO:5) and HSP16.9 (SEQ ID NO:6). It would be immediately apparent to one of ordinary skill in the art to practice similar methods to obtain additional promoter sequences from the upstream regions of genes from plants other than maize and rice that are homologous to the maize or rice RAB17, CA4H, HVA22, HSP17.5, HSP22, or HSP16.9 genes. Thus, without undue experimentation, additional promoters could be obtained from the upstream regions of RAB17, CA4H, HVA22, HSP17.5, HSP22, or HSP16.9 homologous genes from any monocot or dicot plant of interest, including but not limited to, crop plants, wood- or pulp-producing trees, vegetable plants, fruit plants, and ornamental plants (for example, wheat, oat, barley, maize, rye, triticale, rice, ornamental and forage grasses, sorghum, millet, sugarcane, coconut, oil palm, date palm, olive, tree nuts, canola, cotton, safflower, soybean, sugarbeet, buckwheat, sunflower, tea, and coffee; wood- or pulp-producing trees; legumes, lettuce, asparagus, artichoke, celery, carrot, radish, amaranth, the brassicas, edible curcubits, edible alliums, edible members of the Solanaceae, and edible members of the Chenopodiaceae; apple, pear, citrus fruit, apricot, peach, plum, nectarine, banana, pineapple, grape, kiwifruit, papaya, avocado, and berries; and ornamental plants). In an analogous fashion, one skilled in the art could obtain yet additional promoter sequences by searching sequence databases for sequences homologous to the rice promoter sequences disclosed and claimed herein (that is, any of SEQ ID NO:1, SEQ ID NO:2, SEQ ID NO:3, SEQ ID NO:4, SEQ ID NO:5, and SEQ ID NO:6) or the maize promoter sequences disclosed and claimed in U.S. Patent Application Publication Number 2004/0123347. Such additional promoter sequences having promoter activity in plants under conditions of stress, are encompassed and claimed by the present invention.

The regulatory promoter regions isolated from the maize and rice RAB17, CA4H, HVA22, HSP17.5, HSP22, or HSP16.9 genes are thus useful in defining stress-inducible promoters for this invention. Under non-stress conditions (for example, well-watered conditions), these promoters drive expression of the native genes to very low or non-detectable levels. Stress-inducible promoters derived from the 5' regulatory region of RAB17, CA4H, HVA22, HSP17.5, HSP22, or HSP16.9 genes can be used in directing the expression of potentially any gene which one desires to have expressed under conditions of stress (for example, water deficit, cold, heat, salt, pest, disease, nutrient, or other environmental stress). In one embodiment of the invention, stress-inducible promoters derived from the 5' regulatory region of RAB17, CA4H, HVA22, HSP17.5, HSP22, or HSP16.9 genes can be used in directing the expression of potentially any gene which one desires to have expressed when water is limiting during plant growth.

These promoters represent a significant advance in that they are capable of directing stress-regulated expression of transgenes. The stress-inducible nature of the promoters of the invention is advantageous in that it allows expression of a transgene operatively linked to the promoter under conditions of water deficit, cold, heat, salt, pest, disease, nutrient, or other environmental stress, with little to no expression under non-stress conditions (for example, well-watered conditions). By avoiding continuous high-level expression of transgenes, any undesired effects, e.g., disadvantageous traits (for example, yield drag sometimes associated with transgene expression by a constitutive promoter, caused by continual over-expression of transgenes, or ectopic expression in various tissues or at various times) can be minimized or eliminated.

The RAB17, CA4H, HVA22, HSP17.5, HSP22, or HSP16.9 promoter sequences useful in the various aspects of this invention can be derived from any plant of interest, including, but not limited to, economically or agriculturally important plants (for example, wheat, oat, barley, maize, rye, triticale, rice, ornamental and forage grasses, sorghum, millet, sugarcane, wood- or pulp-producing trees, canola, cotton, safflower, soybean, sugarbeet, and sunflower). Non-limiting embodiments of promoter sequences which were isolated from rice to illustrate this invention have nucleic acid sequences given in SEQ ID NO:1 (RAB17 promoter), SEQ ID NO:1 (CA4H promoter), SEQ ID NO:1 (HVA22 promoter), SEQ ID NO:4 (HSP17.5 promoter), SEQ ID NO:5 (HSP22 promoter) and SEQ ID NO:6 (HSP16.9 promoter). A putative TATA box element is identified at about nucleotide 870 and a putative CAAT box element is identified at about nucleotide 838 in SEQ ID NO:1. A putative TATA box element is identified at about nucleotide 1180 and a putative CAAT box element is identified at about nucleotide 1020 in SEQ ID NO:2. A putative TATA box element is identified at about nucleotide 874 and a putative CAAT box element is identified at about nucleotide 757 in SEQ ID NO:3. A putative TATA box element is identified at about nucleotide 205 and a putative CAAT box element is identified at about nucleotide 53 in SEQ ID NO:4. A putative TATA box element is identified at about nucleotide 241 and a putative CAAT box element is identified at about nucleotide 177 in SEQ ID NO:5. A putative TATA box element is identified at about nucleotide 1030 and a putative CAAT box element is identified at about nucleotide 891 in SEQ ID NO:6.

In addition to the unmodified RAB17, CA4H, HVA22, HSP17.5, HSP22, or HSP16.9 promoter sequences of SEQ ID NO:1, SEQ ID NO:2, SEQ ID NO:3, SEQ ID NO:4, SEQ ID NO:5, and SEQ ID NO:6 respectively, the current invention includes derivatives of these sequences and compositions made therefrom. One important application of the RAB17, CA4H, HVA22, HSP17.5, HSP22, and HSP16.9 rice promoters and derivatives thereof is in the construction of DNA constructs designed for introduction into plants by genetic transformation.

Derivative Stress-Inducible Promoters

This invention provides stress-inducible promoters which have been derived from the 5' regulatory regions of the rice RAB17, CA4H, HVA22, HSP17.5, HSP22, or HSP16.9 genes. Derivatives of these promoters may include, but are not limited to, deletions of sequence, single or multiple point mutations, alterations at a particular restriction enzyme site, addition of functional elements, or other means of molecular modification which may enhance, or otherwise alter promoter expression. Techniques for obtaining such derivatives are well known in the art. See, for example, methodologies disclosed in Sambrook and Russell, "Molecular Cloning: A Laboratory Manual", third edition, Cold Spring Harbor Laboratory Press, 2001, incorporated by reference herein. For example, one of ordinary skill in the art may delimit the functional elements within the RAB17, CA4H, HVA22, HSP17.5, HSP22, or HSP16.9 promoters and delete any non-essential elements. Functional elements may be modified or combined to increase the utility or expression of the sequences of the invention for any particular application. For example, a functional region within the RAB17, CA4H, HVA22, HSP17.5, HSP22, or HSP16.9 promoters of the invention could be modified to decrease or increase inducible expression. The means for mutagenizing or creating deletions in a DNA segment encoding an RAB17, CA4H, HVA22, HSP17.5, HSP22, or HSP16.9 promoter sequence of the current invention are well-known to those of skill in the art and are disclosed in detail, for example, in U.S. Pat. No. 6,583,338, which is incorporated herein by reference in its entirety.

It is anticipated that fragments of natural RAB17, CA4H, HVA22, HSP17.5, HSP22, or HSP16.9 promoters that are especially useful for allowing functionality include, but are not limited to:

(1) the about 75 base pair region of 5' UTR region from the transcriptional start site to the ATG (about nucleotide 917 to about 991 of SEQ ID NO:1), the about 150 nucleotide base pair 5' UTR region from the CAAT box to the ATG, including the TATA box (about nucleotide 838 to about 991 of SEQ ID NO:1), the about 80 base pair region from the CAAT box to the transcriptional start site (about nucleotide 838 to about 917 of SEQ ID NO:1), and all sequences and fragments thereof upstream of the CAAT box (from about nucleotide 1 to about 838 of SEQ ID NO:1) of the rice RAB17 promoter; or (2) the 5' UTR region from the transcriptional start site to the ATG, the about 315 nucleotide base pair 5' UTR region from the CAAT box to the ATG, including the TATA box (about nucleotide 1020 to about 1333 of SEQ ID NO:2), the region from the CAAT box to the transcriptional start site, and all sequences and fragments thereof upstream of the CAAT box (from about nucleotide 1 to about 1020 of SEQ ID NO:2) of the rice CA4H promoter; or (3) the about 120 base pair region of 5' UTR region from the transcriptional start site to the ATG (about nucleotide 899 to about 1019 of SEQ ID NO:3), the about 260 nucleotide base pair 5' UTR region from the CAAT box to the ATG, including the TATA box (about nucleotide 757 to about 1019 of SEQ ID NO:3), the about 140 base pair region from the CAAT box to the transcriptional start site (about nucleotide 757 to about 899 of SEQ ID NO:3), and all sequences and fragments thereof upstream of the CAAT box (from about nucleotide 1 to about 757 of SEQ ID NO:3) of the rice HVA22 promoter; or (4) the 5' UTR region from the transcriptional start site to the ATG, the about 370 nucleotide base pair 5' UTR region from the CAAT box to the ATG, including the TATA box (about nucleotide 53 to about 425 of SEQ ID NO:4), the region from the CAAT box to the transcriptional start site, and all sequences and fragments thereof upstream of the CAAT box (from about nucleotide 1 to about 53 of SEQ ID NO:4) of the rice HSP17.5 promoter; or (5) the 5' UTR region from the transcriptional start site to the ATG, the about 160 nucleotide base pair 5' UTR region from the CAAT box to the ATG, including the TATA box (about nucleotide 177 to about 339 of SEQ ID NO:5), the region from the CAAT box to the transcriptional start site, and all sequences and fragments thereof upstream of the CAAT box (from about nucleotide 1 to about 177 of SEQ ID NO:5) of the rice HSP22 promoter; or (6) the about 90 base pair region of 5' UTR region from the transcriptional start site to the ATG (about nucleotide 1092 to about 1180 of SEQ ID NO:6), the about 290 nucleotide base pair 5' UTR region from the CAAT box to the ATG, including the TATA box (about nucleotide 891 to about 1180 of SEQ ID NO:6), the about 200 base pair region from the CAAT box to the transcriptional start site (about nucleotide 891 to about 1092 of SEQ ID NO:6), and all sequences and fragments thereof upstream of the CAAT box (from about nucleotide 1 to about 891 of SEQ ID NO:6) of the rice HSP16.9 promoter.

These and other fragments may be operably linked to a heterologous DNA in a DNA construct and used for plant transformation. The heterologous DNA may include a marker gene or reporter gene useful for testing the promoter activity of the various fragments. It is also anticipated that the sequences and fragments thereof upstream of the CAAT box (from about nucleotide 1 to about 838 of SEQ ID NO:1; from about nucleotide 1 to about 1020 of SEQ ID NO:2; from about nucleotide 1 to about 757 of SEQ ID NO:3; from about nucleotide 1 to about 53 of SEQ ID NO:4; from about nucleotide 1 to about 177 of SEQ ID NO:5; or from about nucleotide 1 to about 891 of SEQ ID NO:6) may be operably linked to heterologous CAAT and TATA boxes or other transcriptional start site sequences and exhibit promoter activity similar or identical to that of the full-length, natural promoters.

Thus, promoters of this invention are not required to have 100% sequence identity to SEQ ID NO:1, SEQ ID NO:2, SEQ ID NO:3, SEQ ID NO:4, SEQ ID NO:5, and SEQ ID NO:6. For instance, effective promoters can include sequences of at least about 100 nucleotides and including about 85% to 100% identity to at least one segment of SEQ ID NO:1, SEQ ID NO:2, SEQ ID NO:3, SEQ ID NO:4, SEQ ID NO:5, and SEQ ID NO:6, or a fragment of any of SEQ ID NO:1, SEQ ID NO:2, SEQ ID NO:3, SEQ ID NO:4, SEQ ID NO:5, and SEQ ID NO:6, e. g., a DNA fragment of at least 100 nucleotides, about 125 nucleotides, about 300 nucleotides, about 500 nucleotides, about 750 nucleotides, or more. In one aspect of the invention the promoters and derivative promoters are characterized as having at least 85% sequence identity, more preferably at least 90% sequence identity or higher, e. g., at least 95% or at least 98% sequence identity with at least a segment of SEQ ID NO:1, SEQ ID NO:2, SEQ ID NO:3, SEQ ID NO:4, SEQ ID NO:5, and SEQ ID NO:6, or a fragment with at least 125 continuous nucleotides within SEQ ID NO:1, SEQ ID NO:2, SEQ ID NO:3, SEQ ID NO:4, SEQ ID NO:5, and SEQ ID NO:6.

Plant Transformation Constructs

The construction of vectors which may be employed in conjunction with plant transformation techniques according to the invention will be known to those of ordinary skill in the art in light of this disclosure. Many approaches or methods have been developed and used for gene cloning. Examples of these are cloning by restriction enzyme digestion and ligation of compatible ends, T-A cloning directly from PCR product, TOPO-attached unidirectional cloning, and recombination-based cloning.

The techniques of the current invention are thus not limited to any particular DNA sequences in conjunction with a rice RAB17, CA4H, HVA22, HSP17.5, HSP22, or HSP16.9 promoter of the invention. For example, a RAB17, CA4H, HVA22, HSP17.5, HSP22, or HSP16.9 promoter alone could be transformed into a plant with the goal of enhancing or altering the expression of one or more genes in the host genome, particularly under water deficit, cold, heat, salt, pest, disease, nutrient, or other environmental stress. Useful heterologous DNA sequences to operably link to the promoter sequences of the invention are exemplified by sequences encoding proteins, polypeptide products, RNA molecules such as antisense RNA molecules, marker genes, or combinations thereof. In certain embodiments, the present inventors contemplate the transformation of a recipient cell with more than one transformation construct, that is to say, a co-transformation. Preferred components suitable for inclusion with vectors used in the current invention include, but are not limited to, regulatory elements including 3' untranslated regions, 5' untranslated regions, enhancers, introns, signal peptide coding sequences, transit peptide coding sequences, selectable marker genes, screenable marker genes, and the like.

A discussion of useful plant transformation constructs which can be prepared by those of ordinary skill in the art can be found among, for example, U.S. Pat. No. 5,641,876 which discloses a rice actin promoter, U.S. Pat. No. 6,429,357 which discloses a rice actin 2 promoter and intron, U.S. Pat. No. 6,084,089 which discloses cold inducible promoters, U.S. Pat. No. 6,140,078 which discloses salt inducible promoters, U.S. Pat. No. 6,252,138 which discloses pathogen inducible promoters, and U.S. Patent Application Publication 2002/0192813A1 which discloses 5', 3', and intron elements useful in the design of effective plant expression vectors, all of which patents and publications are incorporated herein by reference.

In certain embodiments of the invention, transformation of a recipient cell may be carried out with more than one exogenous DNA. The DNA molecules may code for a protein product, or a non-protein product, such as a transfer RNA, an RNA aptamer, anti-sense RNA or hairpin-forming RNA molecule. For example, two or more exogenous coding sequences can be supplied in a single transformation event using either distinct heterologous DNA vectors, or using a single vector incorporating two or more heterologous DNA sequences.

Exogenous Genes for Modification of Plant Phenotypes

This invention provides plants which can express genes to counteract or ameliorate water deficit, cold, heat, salt, pest, disease, nutrient, or other environmental stress. Useful genes for expression especially during conditions of water deficit or other environmental stress, are genes which promote aspects of plant growth or fertility, genes which impart disease resistance, genes which impart pest resistance, and the like. The promoters of this invention which can express genes at a useful level during conditions of stress (for example, water deficit stress), with little if any expression during non-stress conditions (for example, well-watered conditions), are useful for making such plants. In particular, the current invention provides promoters derived from the 5' regulatory region of a RAB17, CA4H, HVA22, HSP17.5, HSP22, or HSP16.9 gene for the expression of selected heterologous DNA in plants.

The choice of a selected DNA for expression in a plant host cell in accordance with the invention will depend on the purpose of the transformation. One of the major purposes of transformation of crop plants is to express any gene which one desires to have expressed during conditions of water deficit, cold, heat, salt, pest, disease, nutrient, or other environmental stress, for imparting a commercially desirable, agronomically important, or end-product trait to the plant. Such traits include, but are not limited to, herbicide resistance, herbicide tolerance, insect resistance, insect tolerance, disease resistance, disease tolerance (viral, bacterial, fungal, nematode), stress tolerance, stress resistance, as exemplified by resistance or tolerance to water deficit, heat, chilling, freezing, excessive moisture, salt stress and oxidative stress, increased yield, food content and value, increased feed content and value, physical appearance, male sterility, female sterility, drydown, standability, prolificacy, starch quantity and quality, oil quantity and quality, protein quality and quantity, amino acid composition, and the like. It is also anticipated that expression of heterologous DNA encoding anti-sense RNAs, RNA aptamers, or other RNA molecules are included as useful means for modifying plant phenotype. An especially useful class of selected DNA for use with the promoters of this invention includes genes which encode a molecule which enhances environmental stress tolerance, for example, genes which enhance water deficit resistance or tolerance when expressed under water deficit conditions.

Alternatively, an exogenous DNA sequence may be designed to down-regulate a specific nucleic acid sequence. This can be accomplished, for example, by operably linking with a promoter, such as a water-deficit-inducible promoter of the invention, an exogenous DNA in an antisense orientation or a DNA designed such that a gene-suppressing RNA molecule (e. g., double-stranded RNA, an RNA aptamer, or anti-sense RNA) is generated upon transcription. Gene suppression may be effective against a native plant gene associated with a trait, e. g., to provide plants with enhanced tolerance to water deficit, cold, heat, salt, pest, disease, nutrient, or other environmental stress. For example, a CA4H promoter of the invention may be operably linked to a heterologous DNA designed such that a gene-suppressing RNA molecule is formed for suppression of a native gene.

Assays of Transgene Expression

To confirm the presence of an exogenous DNA in regenerated plants, a variety of assays may be performed. Such assays include, for example, molecular biological assays such as Southern and Northern blotting and PCR; biochemical assays such as detecting the presence of a protein product, e. g., by immunological means (ELISAs and Western blots) or by enzymatic function; plant part assays such as leaf or root assays; and in some cases phenotype analysis of a whole regenerated plant. Additional assays useful for determining the efficiency of transgene expression and promoter function also include, without limitation, fluorescent in situ hybridization (FISH), direct DNA sequencing, pulsed field gel electrophoresis (PFGE) analysis, single-stranded conformation analysis (SSCA), RNase protection assay, allele-specific oligonucleotide (ASO), dot blot analysis, denaturing gradient gel electrophoresis, RT-PCR, quantitative RT-PCR, RFLP and PCR-SSCP. Such assays are well known to those of ordinary skill in the art.

Methods for Plant Transformation

Suitable methods for plant transformation for use with the current invention are believed to include virtually any method by which DNA can be introduced into a cell, such as by direct delivery of DNA such as by PEG-mediated transformation of protoplasts, by electroporation, by agitation with silicon carbide fibers, by *Agrobacterium*-mediated transformation, and by acceleration of DNA coated particles, etc. Through the application of techniques such as these, maize cells, as well as those of virtually any other plant species, may be stably transformed, and these cells developed into transgenic plants of the invention. Preferred methods of plant transformation include, but are not limited to, microprojectile bombardment as illustrated, for example, in U.S. Pat. Nos. 5,015,580, 5,550, 318, 5,538,880, 6,160,208, 6,399,861, and 6,403,865 and *Agrobacterium*-mediated transformation as illustrated, for example, in U.S. Pat. Nos. 5,635,055, 5,824,877, 5,591,616, 5,981,840, and 6,384,301, all of which are incorporated herein by reference.

The seeds of this invention can be harvested from fertile transgenic plants and be used to grow progeny generations of transformed plants of this invention including hybrid or inbred plant lines including the DNA construct operably linked to any of the stress-inducible promoters of the invention.

Recipient Cells for Transformation

Transformation methods of this invention to provide plants including an exogenous DNA operably linked to the RAB17, CA4H, HVA22, HSP17.5, HSP22, or HSP16.9 promoters are preferably practiced in tissue culture on media and in a controlled environment. "Media" refers to the numerous nutrient mixtures that are used to grow cells in vitro, that is, outside of the intact living organism. A preferred medium is a suspension of various categories of ingredients (salts, amino acids, growth regulators, sugars, buffers) that are required for growth of a cell type of interest. However, it is well known in the art that each specific cell type requires a specific range of ingredient proportions for growth, and an even more specific range of formulas for optimum growth. Rate of cell growth also will vary among cultures initiated with the array of media that permit growth of that cell type.

Recipient cell targets include, but are not limited to, meristem cells, callus, immature embryos, and gametic cells such as microspores, pollen, sperm, and egg cells. It is contemplated that any cell from which a fertile plant may be regenerated is useful as a recipient cell. Callus may be initiated from tissue sources including, but not limited to, immature embryos, seedling apical meristems, microspores, and the like. Those cells which are capable of proliferating as callus also are suitable recipient cells for genetic transformation. The present invention provides techniques for transforming immature embryos and subsequent regeneration of fertile transgenic plants. Practical transformation methods and materials for making transgenic plants of this invention, e. g., various media and recipient target cells, transformation of immature embryos and subsequent regeneration of fertile transgenic plants are disclosed, for example, in U.S. Pat. No. 6,194,636 and U.S. Patent Application Publication Number 2004/0216189, which are incorporated herein by reference.

Production and Characterization of Stably Transformed Plants

After effecting delivery of exogenous DNA to recipient cells, the next steps generally concern identifying the transformed cells for further culturing and plant regeneration. In order to improve the ability to identify transformants, one may employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

It is believed that DNA is introduced into only a small percentage of target cells in any one experiment. In order to provide an efficient system for identification of those cells receiving DNA and integrating it into their genomes, one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS or CP4). Examples of such selectable are illustrated in, for example, U.S. Pat. Nos. 5,550,318, 5,633,435, 5,780,708, and 6,118,047, all of which are incorporated herein by reference.

Cells that survive the exposure to the selective agent, or cells that have been scored positive in a screening assay, may be cultured in media that supports regeneration of plants. Ideally, seed containing the construct of the invention is collected from the transgenic plant. Screenable markers which provide an ability to visually identify transformants can also be employed, e. g., a gene expressing a colored or fluorescent protein such as a luciferase or green fluorescent protein (GFP), or a gene expressing a beta-glucuronidase or uidA gene (GUS) for which various chromogenic substrates are known.

Site Specific Integration or Excision of Transgenes

It is specifically contemplated by the inventors that one can use techniques for the site-specific integration or excision of transformation constructs prepared in accordance with the instant invention. An advantage of site-specific integration or excision is that it can be used to overcome problems associated with conventional transformation techniques, in which transformation constructs typically randomly integrate into a host genome and multiple copies of a construct may integrate. This random insertion of introduced DNA into the genome of host cells can be detrimental to the cell if the foreign DNA inserts into an essential gene. In addition, the expression of a transgene may be influenced by "position effects" caused by the surrounding genomic DNA. Further, because of difficulties associated with plants possessing multiple transgene copies, including gene silencing, recombination and unpredictable inheritance, it is typically desirable to control the copy number of the inserted DNA, often only desiring the insertion of a single copy of the DNA sequence.

Site-specific integration can be achieved in plants by means of homologous recombination. DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events).

A number of different site specific recombinase systems could be employed in accordance with the instant invention, including, but not limited to, the Cre/lox system of bacteriophage P1, the FLP/FRT system of yeast, the Gin recombinase of phage Mu, the Pin recombinase of *E. coli*, and the R/RS system of the pSR1 plasmid. The bacteriophage P1 Cre/lox and the yeast FLP/FRT systems constitute two particularly useful systems for site specific integration or excision of transgenes. In these systems, a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors. The FLP/FRT and Cre/lox recombinase systems have been demonstrated to function efficiently in plant cells. A more thorough discussion of site-specific integration or excision of transgenes may be found in, for example, U.S. Pat. No. 4,959,317 and U.S. Pat. No. 5,527,695, both of which are incorporated herein by reference in their entirety.

Deletion of Sequences Located within the Transgenic Insert

During the transformation process it is often necessary to include ancillary sequences, such as selectable marker or reporter genes, for tracking the presence or absence of a desired trait gene transformed into the plant on the DNA construct. Such ancillary sequences often do not contribute to the desired trait or characteristic conferred by the phenotypic trait gene. Homologous recombination is a method by which introduced sequences may be selectively deleted in transgenic plants.

It is known that homologous recombination results in genetic rearrangements of transgenes in plants. Deletion of sequences by homologous recombination relies upon directly repeated DNA sequences positioned about the region to be excised in which the repeated DNA sequences direct excision utilizing native cellular recombination mechanisms. The first fertile transgenic plants are crossed to produce either hybrid or inbred progeny plants, and from those progeny plants, one or more second fertile transgenic plants are selected which contain a second DNA sequence that has been altered by recombination, preferably resulting in the deletion of the ancillary sequence. The first fertile plant can be either hemizygous or homozygous for the DNA sequence containing the directly repeated DNA which will drive the recombination event.

The directly repeated sequences are located 5' and 3' to the target sequence in the transgene. As a result of the recombination event, the transgene target sequence may be deleted, amplified or otherwise modified within the plant genome. In the preferred embodiment, a deletion of the target sequence flanked by the directly repeated sequence will result. See, for example, U.S. Pat. Nos. 6,580,019 and 6,750,379, both of which are incorporated herein by reference in their entirety, for additional discussion of the deletion of sequences located within a transgenic insert.

Breeding Plants of the Invention

This invention contemplates and claims both plants directly regenerated from cells which have been transformed with a DNA construct of this invention as well as progeny of such plants, e. g., inbred progeny and hybrid progeny of transformed plants. This invention contemplates transgenic plants produced by direct transformation with a DNA construct of this invention and transgenic plants made by crossing a plant having a construct of the invention to a second plant lacking the construct. Crossing can include, for example, the following steps:

(a) plant seeds of the first parent plant (e. g., non-transgenic or a transgenic) and a second parent plant having a transgenic DNA construct;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

It is often desirable to introgress a DNA construct into elite varieties, e. g., by backcrossing, to transfer a specific desirable trait from one source to an inbred or other plant that lacks that trait. This can be accomplished, for example, by first crossing a superior inbred ("A") (recurrent parent) to a donor inbred ("B") (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent "B", then the selected progeny are mated back to the superior recurrent parent "A". After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i. e., one or more transformation events.

Through a series of breeding manipulations, a selected DNA construct may be moved from one line into an entirely different line without the need for further recombinant manipulation. One may thus produce inbred plants which are true breeding for one or more DNA constructs. By crossing different inbred plants, one may produce a large number of different hybrids with different combinations of DNA constructs. In this way, plants may be produced which have the desirable agronomic properties frequently associated with hybrids ("hybrid vigor"), as well as the desirable characteristics imparted by one or more DNA constructs.

Genetic markers may be used to assist in the introgression of one or more DNA constructs of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized. The usefulness of marker assisted selection in breeding transgenic plants of the current invention, as well as types of useful molecular markers, such as but not limited to SSRs and SNPs, are discussed in PCT Application Publication WO 02/062129 and U.S. Patent Application Publications Numbers 2002/0133852, 2003/0049612, and 2003/0005491, each of which is incorporated herein by reference in their entirety.

The ultimate goal in plant transformation is to produce plants which are useful to man. In this respect, transgenic plants created in accordance with the current invention may be used for virtually any purpose deemed of value to the grower or to the consumer. For example, one may wish to harvest seed for planting purposes, or products may be made from the seed itself such as oil, starch, animal or human food, pharmaceuticals, and various industrial products. For example, maize is used extensively in the food and feed industries, as well as in industrial applications. Further discussion of the uses of maize can be found, for example, in U.S. Pat. Nos. 6,194,636, 6,207,879, 6,232,526, 6,426,446, 6,429,357, 6,433,252, 6,437,217, and 6,583,338 and PCT Publications WO 95/06128 and WO 02/057471, each of which is incorporated herein by reference in its entirety.

EXAMPLES

Example 1

Promoter Sequences

This example is a non-limiting example of promoter sequences and derivative promoter sequences of the invention. More specifically, this example illustrates the identification of maize (*Zea mays*) genes which showed increased expression under stress conditions (for example, water deficit) (described in detail in U.S. patent application Ser. No. 10/739,565 to Hinchey et al., filed 18 Dec. 2003 and published as U.S. Patent Application Publication 2004/0123347, incorporated herein by reference in its entirety) and the use of these maize gene sequences to identify and isolate novel stress-inducible promoters from rice.

Maize lines were field-grown under non-irrigated (water-deficit-producing) or irrigated (well-watered) conditions. Water-deficit conditions were achieved by growing in a geographical location in which rainfall was usually limiting, and, if needed, by withholding irrigation. Leaf samples were taken from plants before the tassel stage for each condition. Leaf tissue was used to determine water potential. Messenger RNAs (mRNAs) were isolated from the water deficit (i.e., having a water potential less than about −0.7 megaPascals) and well-watered samples and was analyzed for differences using transcriptional profiling array methods. A number of mRNAs were found to show differences in accumulation, to either higher or lower levels in the plants, depending upon the water treatment. Array samples were selected that demonstrated at least a 3-fold increase in mRNA accumulation under water deficit conditions versus well-watered conditions. The candidate water-deficit-inducible genes were identified as a rab17 protein (RAB17) gene, an HVA22 gene (HVA22), a gene encoding cinnamic acid 4-hydroxylase (CA4H), and heat shock protein 17.5, 22 and 16.9 genes (HSP17.5, HSP22 and HSP16.9, respectively).

Under non-stress (well-watered) conditions, the HSP17.5 gene was found to be expressed to low levels in spikelet, shank, cob, and internode tissues; the CA4H gene was expressed to low levels in root and cob tissues. Low levels of HSP22 gene expression was found in the internode, cob, endosperm, kernel, shank, silk, and spikelet tissues. The HVA22, RAB17 and HSP16.9 genes, also under well-watered conditions, were found to have no expression in any of the maize tissues tested. Table 1 shows the fold-induction observed for the transcripts of these genes in maize leaf tissue under stress (water deficit) conditions.

TABLE 1

| Gene | Measured increase in mRNA expression |
|---|---|
| RAB17 | 8.2 x |
| CA4H | 3.4 x |
| HVA22 | 3.8 x |
| HSP17.5 | 4.3 x |
| HSP22 | 3.1 x |
| HSP16.9 | 3.2 x |

The protein coding sequences of the maize RAB17, CA4H, HVA22, HSP17.5, HSP22, or HSP16.9 genes were used to identify novel promoters from homologous genes in rice. A similar search for homologous sequences could be performed using sequence data for any monocot or dicot plant of interest, including but not limited to, crop plants, wood- or pulp-producing trees, vegetable plants, fruit plants, and ornamental plants (for example, wheat, oat, barley, maize, rye, triticale, rice, ornamental and forage grasses, sorghum, millet, sugarcane, coconut, oil palm, date palm, olive, tree nuts, canola, cotton, safflower, soybean, sugarbeet, buckwheat, sunflower, tea, and coffee; wood- or pulp-producing trees; legumes, lettuce, asparagus, artichoke, celery, carrot, radish, amaranth, the brassicas, edible curcubits, edible alliums, edible members of the Solanaceae, and edible members of the Chenopodiaceae; apple, pear, citrus fruit, apricot, peach, plum, nectarine, banana, pineapple, grape, kiwifruit, papaya, avocado, and berries; and ornamental plants). Using search tools known to those of skill in the art (BLAST, BLASTX, TBLASTN, etc.), full length sequences for maize genes RAB17, CA4H, HVA22, HSP17.5, HSP22, or HSP16.9 DNA were translated and used in searches against rice protein sequence databases. Results from the protein sequence comparisons were used to identify the corresponding full-length rice protein coding DNA sequence and the full length rice protein coding DNA sequences were used in searches against rice genomic DNA databases. To confirm rice protein coding DNA sequences showing homology to maize protein coding DNA sequences, the rice coding sequences were used in searches against maize sequence databases. Rice sequences showing homology to the maize sequences were selected, the coding regions determined and the genomic sequences upstream of the coding regions were identified as 5' regulatory promoter regions. In some instances, a portion of the first exon was retained in the proposed promoter sequence; in other instances a portion of the untranslated leader sequence was excluded. Rice stress-inducible promoters were isolated from genomic clones using PCR amplification and sequencing of the PCR-amplified, isolated DNA.

One skilled in the art would realize that a variety of primers could be designed using the gene coding sequences, genomic DNA sequences, or sequences provided herein in SEQ ID NO:1 through SEQ ID NO:6, to amplify and isolate DNA for sequencing and assaying for promoter activity, and thus obtain additional novel promoter sequences of the instant invention, including promoter sequences which include at least 100 contiguous nucleotides which are identical or substantially identical to at least one segment of any of SEQ ID NO:1, SEQ ID NO:2, SEQ ID NO:3, SEQ ID NO:4, SEQ ID NO:5, and SEQ ID NO:6.

Example 2

DNA Constructs

This example is a non-limiting example of DNA constructs of the present invention. More particularly, this example illustrates the construction of transformation vectors comprising a stress-inducible 5' regulatory region derived from the rice RAB17 (SEQ ID NO:1), CA4H (SEQ ID NO:2), HVA22 (SEQ ID NO:3), HSP17.5 (SEQ ID NO:4), HSP22 (SEQ ID NO:5), or HSP16.9 (SEQ ID NO:6) promoters. In each case, the full length promoter, as well as fragments of the promoter, are isolated and operably linked to a reporter gene, or any other gene, for testing promoter activity.

A non-limiting example of a preferred reporter gene for monitoring promoter activity is the uidA screenable marker gene (Jefferson et al., *Proc. Natl. Acad. Sci. USA,* 83(22): 8447-8451, 1986; Jefferson, *Plant Mol. Biol. Rep.,* 5:387-405, 1987). As is well known to those skilled in the art, when the uidA gene is operably linked to a functional promoter, the uidA gene product (commonly referred to as GUS), in the presence of the appropriate buffers and substrates, results in a blue pigmentation in cells and tissues expressing the uidA gene. In certain embodiments, it is also preferred to operably link the reporter gene to a 3' untranslated region, for example, a nos, pinII, or T7 3' UTR. In addition, the promoter in testing can be operably linked to an intron, such as a rice actin 1 intron 1 (U.S. Pat. No. 5,641,876, which is incorporated herein by reference in its entirety) or a rice actin 2 intron 1 (U.S. Pat. No. 6,429,357, which is incorporated herein by reference in its entirety) or the hsp70 intron from the maize hsp70 gene (U.S. Pat. No. 5,424,412, which is incorporated herein by reference in its entirety).

Exemplary constructs therefore, comprise, in order from 5' to 3', one of the rice RAB17 (SEQ ID NO:1), CA4H (SEQ ID NO:2), HVA22 (SEQ ID NO:3), HSP17.5 (SEQ ID NO:4), HSP22 (SEQ ID NO:5), or HSP16.9 (SEQ ID NO:6) promoters of the instant invention, or a fragment thereof, operably linked to a uidA reporter gene which is operably linked to a 3' UTR. Other constructs comprise, for example, in order from 5' to 3', one of the rice RAB17 (SEQ ID NO:1), CA4H (SEQ ID NO:2), HVA22 (SEQ ID NO:3), HSP17.5 (SEQ ID NO:4), HSP22 (SEQ ID NO:5), or HSP16.9 (SEQ ID NO:6) promoters of the instant invention, or a fragment thereof, operably linked to an intron, operably linked to the uidA reporter gene, operably linked to a 3' UTR.

Plasmid or other vectors comprising one of the promoters of the present invention operably linked to a reporter gene, or any other heterologous sequence, are useful for transformation of plants. In addition, the promoters of the present invention operably linked to a reporter gene, or any other heterologous sequence, may be cloned into the appropriate vector for *Agrobacterium*-mediated or microparticle bombardment transformation of plant cells. Furthermore, isolated fragments of the vectors, especially those comprising the promoter and a selected heterologous DNA are useful in plant transformation. Derivative promoters of the invention (as described above under the heading "Derivative Stress-Inducible Promoters") can be used in similar fashion to transform plants.

Example 3

Transgenic Plants

This example is a non-limiting example of methods to provide transgenic plants of the present invention. More particularly, this example illustrates biolistic transformation of maize (corn) with DNA constructs comprising stress-inducible promoters. Biolistic transformation involves the adherence of the selected DNA to microparticles which are then introduced into recipient cells at high velocity. The bombarded cells are then allowed to recover and regenerate on various media until they are of suitable condition for regeneration into plants, preferably fertile plants. Biolistic transformation methods for maize are known to those of skill in the art.

DNA coated microprojectiles are prepared with adherent DNA constructs prepared as in Example 2 and the particles are bombarded into maize cells. Fertile transgenic plants are produced from transformed maize cells. Regenerated R0 and R1 plants (or plants from any other generation of interest) from a number of independent transformation events are assayed for GUS activity by histochemical staining, thus indicating the expression of the uidA reporter gene operably linked to one of the promoters of the invention and thus the desired promoter activity. UidA reporter gene expression in the transgenic plants is assayed under water deficit and well-watered conditions. GUS staining, indicative of uidA gene expression, is higher in transformed plants under water deficit conditions.

Example 4

Transgenic Plants

This example is a non-limiting example of methods to provide transgenic plants of the present invention. More particularly, this example illustrates *Agrobacterium tumefaciens*-mediated transformation of maize with constructs comprising water-deficit-inducible promoters, such as one of the rice RAB17 (SEQ ID NO:1), CA4H (SEQ ID NO:2), HVA22 (SEQ ID NO:3), HSP17.5 (SEQ ID NO:4), HSP22 (SEQ ID NO:5), or HSP16.9 (SEQ ID NO:6) promoters of the instant invention, or a fragment thereof, or any derivative promoters of the invention (as described above under the heading "Derivative Stress-Inducible Promoters"). Methods of *Agrobacterium*-mediated transformation of maize cells and other monocots are known and various strains of *Agrobacterium* may be used, such as strain ABI. In some embodiments, an *Agrobacterium tumefaciens* binary vector system is preferably used to transform maize. In other embodiments, alternative vector systems can be used, for example, co-integrating Ti plasmid vectors are known in the art and could be used to transform maize. A binary vector comprising one or more genes of interest may be introduced into a disarmed *Agrobacterium* strain using electroporation or triparental mating. A binary vector may contain, for example, a selectable marker gene, a screenable marker gene, and/or one or more genes that confer a desirable phenotypic trait on the transformed plant. Binary vectors useful for the transformation of plants are well known to those of skill in the art. Preferred methods and use of *Agrobacterium*-mediated transformation are illustrated in U.S. Pat. Nos. 5,635,055, 5,824,877, 5,591,616, 5,981,840, and 6,384,301, all of which are incorporated herein by reference.

Example 5

Promoter Activity

This example is a non-limiting example of techniques to analyze activity of promoters of the present invention. More particularly, this example illustrates the analysis of rice RAB17, CA4H, HVA22, HSP17.5, HSP22, or HSP16.9 promoter expression in fertile transgenic maize (see also U.S. Patent Application Publication Number 2004/0123347, which is incorporated herein by reference in its entirety). Regenerated plants from a number of independent transformation events are assayed for GUS activity by histochemical staining, thus indicating the expression of the uidA reporter gene operably linked to one of the rice RAB17 (SEQ ID NO:1), CA4H (SEQ ID NO:2), HVA22 (SEQ ID NO:3), HSP17.5 (SEQ ID NO:4), HSP22 (SEQ ID NO:5), or HSP16.9 (SEQ ID NO:6) promoters of the instant invention. Similarly, expression of the uidA reporter gene operably linked to a derivative promoter of the invention (as described above under the heading "Derivative Stress-Inducible Promoters") can be assayed. The GUS expression patterns are examined in stably transformed R0 maize plants produced from the transformation procedure, and are also examined in the R1 generation (or other generations of interest) of transformed plants. A number of different tissues are examined, including, but not limited to, leaves, male and female reproductive tissues, and roots. UidA reporter gene expression in transgenic plants, as driven by one of the rice RAB17 (SEQ ID NO:1), CA4H (SEQ ID NO:2), HVA22 (SEQ ID NO:3), HSP17.5 (SEQ ID NO:4), HSP22 (SEQ ID NO:5), or HSP16.9 (SEQ ID NO:6) stress-inducible promoters, or any derivative promoter of the invention (as described above under the heading "Derivative Stress-Inducible Promoters"), is assayed under stress (for example, water deficit) and non-stress (for example, well-watered) conditions. It is expected that GUS staining, indicative of uidA gene expression, will be low or undetectable in transformed plants under non-stress conditions, whereas under stress conditions, GUS will accumulate to higher levels due to increased gene expression as driven by one of the stress-inducible promoters of the invention.

In a similar fashion, uidA reporter gene expression in transgenic plants, as driven by one of the rice RAB17 (SEQ ID NO:1), CA4H (SEQ ID NO:2), HVA22 (SEQ ID NO:3), HSP17.5 (SEQ ID NO:4), HSP22 (SEQ ID NO:5), or HSP16.9 (SEQ ID NO:6) stress-inducible promoters, or any derivative promoter of the invention (as described above under the heading "Derivative Stress-Inducible Promoters"), may be assayed under stress conditions other than water deficit, such as, but not limited to, cold, heat, pest, disease, or nutrient stress. Results are expected to be similar to that seen under water deficit condition in the corresponding transgenic plants.

In addition to examining GUS staining patterns in transgenic plants under various conditions, leaf disk assays can be used to conveniently determine the expression of the stress-inducible promoters of the invention in stressed tissues. In one non-limiting embodiment, disks of leaf tissue from maize plants comprising a reporter gene (uidA) are subjected to solutions (such as hormone-, salt-, or PEG-containing solutions), or to conditions such as heat or cold, to mimic a water deficit, salt, or other stress conditions. For example, disks are floated on solutions comprising hormones (for example, 100 micromolar abscisic acid), or saline (for example, 250 millimolar NaCl), or water of the appropriate temperature to simulate stress, for several minutes to several hours, and stained for GUS expression.

Expression of the promoters of the invention can also be monitored at the transcript level. For example, RNA is extracted from leaf tissues from control and treated samples. RT-PCR is carried out as is known in the art, using primers and detection methods designed to specifically identify the mRNA transcript produced by the sequences operably linked to a promoter of the present invention (see, for example, U.S. patent application Ser. No. 10/739,565 to Hinchey et al., filed 18 Dec. 2003 and published as U.S. Patent Application Publication 2004/0123347, which is incorporated herein by reference in its entirety).

Additional expression analysis of promoter activity may be carried out. For example, transgenic plants comprising a reporter gene or an exogenous gene, operably linked to a promoter of the present invention, may be subjected to stress or non-stress conditions in a field as described in Example 1. Examination of the expression of the reporter gene, or other sequence operably linked to a promoter of the instant invention, or a characteristic bestowed on the transgenic plant by the transgene (for example, plant morphology, growth rates, yield, and the like) provides information as to the expression of the water-deficit-inducible promoter under the test and control conditions.

In a controlled environment such as a greenhouse, stress may be imposed upon the plants using a variety of assay conditions. In one non-limiting example, water deficit stress may be simulated by techniques including, but not limited to, germinating seed under water deficit conditions, or imposing water deficit conditions on seedlings or on plants at any stage of development. Water deficit can be induced by withholding or limiting water, or by application of solutions which induce or simulate water deficit (such as saline or PEG solutions).

Any number of parameters may be measured to determine increased tolerance to water deficit, cold, heat, salt, pest, disease, nutrient, or other environmental stress, such as measuring plant height, leaf length, number of leaves, root length, root mass, shoot mass, seed set, number of seed, yield, photosynthesis, chlorophyll, leaf temperature, turgor pressure, osmotic potential, amount of pollen, silking, germination, and the like. In one preferred embodiment of the current invention, maize plants are transformed with a maize or rice stress-inducible promoter operably linked to an exogenous DNA, the product of which is expected to impart increased tolerance to and increased yield under stress conditions, such as water-deficit conditions.

All of the materials and methods disclosed and claimed herein can be made and used, as instructed by the above disclosure, and without undue experimentation, by a person of ordinary skill in the art. Although the materials and methods of this invention have been described in terms of preferred embodiments and illustrative examples, it will be apparent to those of skill in the art that variations may be applied to the materials and methods described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the concept, spirit, and scope of the invention as further defined by the appended claims.

What is claimed is:

1. A transgenic plant having in its genome an exogenous DNA construct comprising a promoter operably linked to a heterologous DNA, wherein said promoter comprises SEQ ID NO:5.

2. The transgenic plant according to claim 1, wherein said promoter is operably linked to a heterologous DNA which encodes a molecule imparting at least one characteristic selected from the group consisting of insect resistance or tolerance; viral, bacterial, fungal, or nematode disease resistance or tolerance; herbicide resistance or tolerance; enhanced grain composition or quality; enhanced nutrient transporter functions; enhanced nutrient utilization; enhanced environmental stress tolerance or resistance; reduced mycotoxin contamination; male sterility; female sterility; a selectable marker phenotype; a screenable marker phenotype; a negative selectable marker phenotype; a stress-responsive transcription factor; altered plant agronomic characteristics; enhanced kernel development; enhanced embryo development; enhanced general production or protection of next-generation tissues; enhanced grain agronomic characteristics; enhanced grain processing characteristics; and a combination thereof.

3. The transgenic plant according to claim 1, wherein said heterologous DNA transcribes to RNA imparting gene suppression of at least one gene in said transgenic plant.

4. The transgenic plant according to claim 3, wherein said heterologous DNA transcribes to double-stranded RNA for suppressing at least one gene in said transgenic plant during stress conditions.

5. The transgenic plant according to claim 1, selected from the group consisting of crop plants, wood- or pulp-producing trees, vegetable plants, fruit plants, and ornamental plants.

6. The transgenic plant according to claim 1, selected from the group consisting of wheat, oat, barley, maize, rye, triticale, rice, ornamental and forage grasses, sorghum, millet, sugarcane, coconut, oil palm, date palm, olive, tree nuts, canola, cotton, safflower, soybean, sugarbeet, buckwheat, sunflower, tea, and coffee; wood- or pulp-producing trees; legumes, lettuce, asparagus, artichoke, celery, carrot, radish, amaranth, the brassicas, edible curcubits, edible alliums, edible members of the Solanaceae, and edible members of the Chenopodiaceae; apple, pear, citrus fruit, apricot, peach, plum, nectarine, banana, pineapple, grape, kiwifruit, papaya, avocado, and berries; and ornamental plants.

7. Seed from a transgenic plant of claim 1, wherein said seed contains said exogenous DNA construct.

8. A DNA construct comprising a promoter operably linked to a heterologous DNA wherein said promoter comprises SEQ ID NO:5.

9. The DNA construct according to claim 8, wherein said promoter is operably linked to a heterologous DNA which encodes a molecule imparting at least one characteristic selected from the group consisting of insect resistance or tolerance; viral, bacterial, fungal, or nematode disease resistance or tolerance; herbicide resistance or tolerance; enhanced grain composition or quality; enhanced nutrient transporter functions; enhanced nutrient utilization; enhanced environmental stress tolerance or resistance; reduced mycotoxin contamination; male sterility; female sterility; a selectable marker phenotype; a screenable marker phenotype; a negative selectable marker phenotype; a stress-responsive transcription factor; altered plant agronomic characteristics; enhanced kernel development; enhanced embryo development; enhanced general production or protection of next-generation tissues; enhanced grain agronomic characteristics; enhanced grain processing characteristics; and a combination thereof.

10. An isolated DNA comprising the nucleotide sequence of SEQ ID NO:5.

* * * * *

SEQUENCE LISTING

```
<160> NUMBER OF SEQ ID NOS: 6

<210> SEQ ID NO 1
<211> LENGTH: 991
<212> TYPE: DNA
<213> ORGANISM: Oryza sativa

<400> SEQUENCE: 1
tgcttgccct tgtcctcatg tacacaatca gcttgcttat ctctcccata ctggtcgttt      60
gtttcccgtg gccgaaatag aagaagacag aggtaggttt tgttagagaa ttttagtggt     120
attgtagcct atttgtaatt ttgttgtact ttattgtatt aatcaataaa ggtgtttcat     180
tctattttga ctcaatgttg aatccattga tctcttggtg ttgcactcag tatgttagaa     240
tattacattc cgttgaaaca atcttggtta agggttggaa cattttatc tgttcgtgaa      300 acatccgtaa tattttcgtt gaaacaattt ttatcgacag caccgtccaa caatttacac     360
caatttggac gtgtgataca tagcagtccc caagtgaaac tgaccaccag ttgaaaggta     420
tacaaagtga acttattcat ctaaaagacc gcagagatgg gccgtgggcc gtggcctgcg     480
```

```
aaacgcagcg ttcaggccca tgagcattta ttttttaaaa aaatatttca caacaaaaaa      540
gagaacggat aaaatccatc gaaaaaaaaa actttcctac gcatcctctc ctatctccat      600
ccacggcgag cactcatcca aaccgtccat ccacgcgcac agtacacaca catagttatc      660
gtctctcccc ccgatgagtc accacccgtg tcttcgagaa acgcctcgcc cgacaccgta      720
cgtggcgcca ccgccgcgcc tgccgcctgg acacgtccgg ctcctctcca cgccgcgctg      780
gccaccgtcc accggctccc gcacacgtct ccctgtctcc ctccacccat gccgtggcaa      840
tcgagctcat ctcctcgcct cctccggctt ataaatggcg ccaccacct tcacctgctt       900 gcacaccaca gcaagagcta agtgagctag ccactgatca gaagaacacc tcgatctccg      960
agagtttttt ttcagcttta gcttaagcag g                                    991

<210> SEQ ID NO 2
<211> LENGTH: 1500
<212> TYPE: DNA
<213> ORGANISM: Oryza sativa

<400> SEQUENCE: 2
tttgatttgg gacaaaaggt tggtgaaatg gacatatttt cacatatata tatgctatat       60
ttttcttctc agtttaccga aaagatgtac ccttatatct cgtcatcgat tttgggtcag      120
gccagaaaac cattggtaac agaatatatg catagttttc tttatcaata aaattaatgt      180
tttatttaaa aatcgataaa ggaactttt  acaaaattag gctagaaatg gtctgtctat      240
tatgacaagg taaacttttg cgacattaat ttggatggca acttcaacaa ttcaaattgt      300
cgttgtccac aaatctcttg gttgtagaag acccacgcgt ctgcaacatt tttgcgccga      360
aaacttaata cataaacttg atttgttggg atacatggtg cagaagatac gatcattaat      420
aattcaaaca gtgcatttca tggtccaact gactgccacg tcattgaacc cgtaatcatt      480
cgctaagcca atcaaattg  gcctcaaatg aattttcagc acgacttttt acgccccaaa      540
aacctagtac tccctccagt tggaaatgta ccctaccaag aaacttgtgt ccgtcacgac      600
gcctgtatca tcaatctagt cctcttttgt aacaaaataa ttttagaaga tttcttttaa      660
tgccgtagaa attaaattaa tcctaatgaa aatcatgtaa aactcacccg ttataaaatg      720
tcactaaccc cctacacggt tggtgtcctc tttgtagccg aaatgcctcc tctttggcca      780
ctgcatctcc acccattttt caaacatctc caactaactt tttgttccat ttgcaaaaat      840
gcaaaatgcg aaatgttaac ttcacacaca ccccccttacc actacaaaac tctcaccaac      900
cccaatctag ctatcagttc agaaagcacc ttcccttctt tccctattag agcaagtcta      960
atagtacagc tcactactag cttcaatta  tctataacca atctaatagt caattcatac     1020
aatagttgct tattatacta ttaatatatg gtctcacctg tcatacacac agtgtgtctt     1080
atagtccgtg ctgcagctgg ctacatatct gtagcctgct agtcttctct ctcatcgttt     1140
atctcattaa aaatatgttta tagctggcta atagcttgct aatagcatgc tattgtacct     1200
gctcttacca ccttctttcc cttttggcaa atggcaatga gtgcaaaaat gcttggaaaa     1260
ataacccccc ccccccacc  cccacctgat tatttccagt agggccaaaa tccgggccca     1320
cgtccgcaac ccatgtgggc cccacatccc ccacaccaac cctctgcacc caaaatcccc     1380
atccccccac tatatataat cccgccgtt  ggatcatcgc cctcagcaga gcagcgcatc     1440
tgcatccaaa accaaaccca aactcgtctt ctccaccgga gcagagcagc ggcggcggca     1500

<210> SEQ ID NO 3
<211> LENGTH: 1019
```

<212> TYPE: DNA
<213> ORGANISM: Oryza sativa

<400> SEQUENCE: 3

```
aatataccat tcgctaaaaa atttgatttt tctatgacgg agaaagcagt agtgtaagca    60
gagcgcccgt aaacatatcc tcacttttgg ttcatctcat attttgtaa gatggaggaa   120
acatgagtga aattagagca ccctgtaaac atatcctcat tttggttcgt ctatcagtca   180
cgtaactttg ttatttctgt cggttaccta gtactaatac ctaagatgat aatccactgt   240
aatgggaaga tgagcacggt tttatatctg aaactgaaaa tgggtctgtt ggtcataaaa   300
cttactacct ccgtttcgaa atatatcaaa ctagcttgta ttagattaga cacgatctat   360
tattcaattt ggacagagtc catatagcta tgatatgctt actatttcat attgctttca   420
tgaacttaac ttaaagtttt ggaccacaat gaaagtttca gttcatatca tatggcatac   480
tacttctatt cttttttttt tgttaaaaaa aaactggagc tctcaatttt tttaaagttt   540
gtcctgttac aattttaatc agttctttat tattcctctc cacatcaaca attttcctc    600
gatgatccgg ttcccttttg acctcactgc actgtcccag atctctcatt aatccaaccc   660
agaaaaaaaa aacagtacaa aataaaatac acaagattca acaaagcaac ctgacctggt   720
cggtgctgta ccacgtggca tctcccctcc atgtcccaat cacttcgaga dacaaaagaa   780
acactcctcc agtggcatcc tgccatgtgt cctccattct tgtacttaat ctcttcttat   840
ttaaggcctc ataatctctt gctttcccctt ccctagtaaa tcaagaaca caaagcatcc   900
aaaacaacac caggaaactt cttttcaatc gatcactcca ctggtgagta gtgagtggct   960
agtgactggt cagttcatca cttgtgaagg ttttgcaatc aggaaaagtt cagaagatc   1019
```

<210> SEQ ID NO 4
<211> LENGTH: 733
<212> TYPE: DNA
<213> ORGANISM: Oryza sativa

<400> SEQUENCE: 4

```
tagcatatat aaaatcattt gtcagagtga acaacacat ccaaattaat gacaaatata    60
aattactaat ctactttgat ccatctcatc attttaaag aaaatactaa atccattaa    120
aagatcattt tggaaaatta aacttttatt gaaaataaac taactcatgt aaaattatac   180
cgttttcctg ttacatgtac aggatataaa ttaacagcgc gccttttggc gcgctgattt   240
tctagtcgaa aagttaaacc ggggtataag tgtagcacct tcgctccact caaagaaaat   300
gtaagccgaa gacttgagaa gcttccagaa tccagagatc gcagcagaaa aggagcgaac   360
aaggcaaacc tctcaaagga aaaagaaaa ataataaagg aggaaacctg tcaaacacca   420
ccctatgaca agtgggtccc actcgaacca accgtacggc ccccccaccc aaacccgctc   480
cccctcgct ccgaaaatat ccacctctct agatctttct cgtcgcaaac gcccttccgc    540
cccgcctcg ccgcgcccat tccaccacct ttccgaacct tccactccct tccagactcc    600
acccccacgt caccccctat taaaccctc ctcccaccga gcaatcaagc gacaagatcg    660
agaagccaca aaccccagcg cgatccgagg tagaagaaga agaagaagaa gaagaagaag   720
aggcgatcga gag                                                     733
```

<210> SEQ ID NO 5
<211> LENGTH: 339
<212> TYPE: DNA
<213> ORGANISM: Oryza sativa

```
<400> SEQUENCE: 5
gttcgtgact tttggcaagg gatcgaatcg gaagcgaatg ggtgggccca aaacgggccg      60
gttattttac tgggactaaa gatatcggcc catctgaatt gtgcgttccg ccggataagg     120
gataactgaa ggcggcgctc agtcccgcgc cttctggaac cttcccgtgg aagggcata     180 cagccttgca gcggcagctt ccggaagctt ctgaattctt ctccaagatt tgccgcgacg    240
ataaatcctc tcgtttctcc gctcgctgat tcattctcaa cgcaaaatcc aaagataag    300 cacagttacg cggcgagagc gagagaggag tggagagcc                           339

<210> SEQ ID NO 6
<211> LENGTH: 1180
<212> TYPE: DNA
<213> ORGANISM: Oryza sativa

<400> SEQUENCE: 6
aaaacctctt ctttaacatg taaacgacct ggaggatgtc aactctgaca cgctggcgaa     60
atcatccacc tatgtctttg ccgcggtata ggatgaacat gggtagagaa aaaaatcggg    120
gtgatccaaa gtgcaataga cgtgacccaa aaagtgtaat tcactaaaaa aaacttacca    180
acgaagcaat gctttggcag tgattttttac cttcagtca tgggcatgac ctgcattgta    240
aaataacgtg gttgtgaatt caaactcaaa tgtgttttc tttcacaagt tgccgttaaa    300
aatatgtttc gcaagagact cactgctccc agtgaaagca gtgaattgaa gcattcccga    360
aacccactgg aatgatctag tactcactct acgatgtaca gtgaagtaat acttcaaaac    420
tggtgtaatt tggtatgcca aaaggactcc atagtttcac gacatatttc caaacggttc    480
aggatcagta ctgcccatct gcctggggcc cacactagcg ggcaattggt tctcgtagtt    540
tctcgttctc aatcaatcat tccatactcg ctatcccctc catcacagaa taaatgcaac    600
aatgagtttc cgtgtacaaa tttaatcgtt cgtcttattt aaaatatttt ttaaaaaact    660
aaaaaacaaa agtcacgcat aaagtactat tcatgtttta taatctaata acagtataaa    720
tactaatcat aaaaaaaaat tcaaataaga tggacgatta aagttgaaca ctgaaattca    780
tggctgcttt tgttttgaga ctgagggagt acacgataag atttgatcgc aatcaaagta    840
acctacatca aagaagcaag atatgtgggg gaaaaatgaa tactctagag caaattaagg    900
tgagccccgc tttgtagagg ctgatggagt actggagcga cggaagcgaa gcagatcgag    960
tgtgctgtaa agcgaaacga gcaagaacca gagaagtcca gagatttcag gacagattag   1020
ttgtgaacct ataaatatcc tgcctcattc cccaacctcc atccatcgag ccaagactga   1080
agcatttgat cgagctccaa acaaacactc gttccaaact tcctccaatc cacttcatac   1140
aaagaaacct aagcagctag cgatccacga caaaccaaca                         1180
```